(12) United States Patent
Bertozzi et al.

(10) Patent No.: US 9,303,068 B2
(45) Date of Patent: Apr. 5, 2016

(54) D-AMINO ACID DERIVATIVE-MODIFIED PEPTIDOGLYCAN AND METHODS OF USE THEREOF

(71) Applicant: The Regents of the University of California, Oakland, CA (US)

(72) Inventors: Carolyn R. Bertozzi, Berkeley, CA (US); Mary Sloan Siegrist Palmore, Berkeley, CA (US); John C. Jewett, Berkeley, CA (US); Chelsea G. Gordon, Berkeley, CA (US); Peyton Shieh, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/092,262

(22) Filed: Nov. 27, 2013

(65) Prior Publication Data
US 2014/0170183 A1    Jun. 19, 2014

Related U.S. Application Data

(60) Provisional application No. 61/731,986, filed on Nov. 30, 2012.

(51) Int. Cl.
| | |
|---|---|
| A61K 39/35 | (2006.01) |
| C07K 9/00 | (2006.01) |
| A61K 47/48 | (2006.01) |
| C12Q 1/02 | (2006.01) |
| C07K 14/47 | (2006.01) |
| C12Q 1/18 | (2006.01) |

(52) U.S. Cl.
CPC ............... *C07K 9/00* (2013.01); *A61K 47/4833* (2013.01); *A61K 47/48246* (2013.01); *C07K 9/001* (2013.01); *C07K 14/4725* (2013.01); *C12Q 1/025* (2013.01); *C12Q 1/18* (2013.01)

(58) Field of Classification Search
None
See application file for complete search history.

(56) References Cited

U.S. PATENT DOCUMENTS 8,303,966 B2   11/2012   Lin et al.

OTHER PUBLICATIONS

Kuru et al (Agnew. Chem. Int. Ed. Published online Oct. 2012. 51: 12519-12523).*
Turner et al (Infect Immun. Oct. 1999; 67(10): 5486-5489).*
Shieh et al (J. of the Amer. Chem. Society (JACS). published Oct. 2012. 134: 17428-17431).*
http://onlinelibrary.wiley.com/doi/10.1002/anie.201206749/abstract. 2012.*
Cava et al., "Distinct pathways for modification of the bacterial cell wall by non canonical D-amino acids", The EMBO Journal, 2011, 30(16):3442-3453.
Devaraj et al., "Biomedical Applications of Tetrazine Cycloadditions", Accounts of Chemical Research, 2011, 44 (9):816-827.
Kaya et al., "A Genetically Encoded Norbornene Amino Acid for the Mild and Selective Modification of Proteins in a Copper-Free Click Reaction", Angew Chem Int Ed, 2012, 51:4466-4469.
Lim et al., "Photoinducible Bioorthogonal Chemistry: A Spatiotemporally Controllable Tool to Visualize and Perturb Proteins in Live Cells", Accounts of Chemical Research, 2011, 44(9):828-839.

* cited by examiner

*Primary Examiner* — Jennifer Graser
(74) *Attorney, Agent, or Firm* — Bozicevic, Field & Francis, LLP; Paula A. Borden; Glenn J. Foulds

(57) ABSTRACT

The present disclosure provides modified bacteria and modified peptidoglycan comprising modified D-amino acids; compositions comprising the modified bacteria or peptidoglycan; and methods of using the modified bacteria or peptidoglycan. The modified D-amino acids include a bioorthogonal functional group such as an azide, an alkyne or a norbornene group. Also provided are modified peptidoglycans conjugated to a molecule of interest via a linker.

15 Claims, 4 Drawing Sheets

D-AMINO ACID DERIVATIVE-MODIFIED PEPTIDOGLYCAN AND METHODS OF USE THEREOF

CROSS-REFERENCE

This application claims the benefit of U.S. Provisional Patent Application No. 61/731,986, filed Nov. 30, 2012, which application is incorporated herein by reference in its entirety.

STATEMENT REGARDING FEDERALLY SPONSORED RESEARCH

This invention was made with government support under Grant No. R01-AI051622 awarded by the National Institute of Health. The government has certain rights in the invention.

INTRODUCTION

Peptidoglycan (PG) is an essential component of the bacterial cell wall. Although experiments with organisms in vitro have yielded a wealth of information on PG synthesis and maturation, it is unclear how these studies translate to bacteria replicating within host cells.

There is a need in the art for methods of identifying agents that inhibit PG synthesis, e.g., in pathogenic bacteria.

SUMMARY

The present disclosure provides modified bacteria and modified peptidoglycan comprising modified D-amino acids; compositions comprising the modified bacteria or peptidoglycan; and methods of using the modified bacteria or peptidoglycan. The modified D-amino acids include a bioorthogonal functional group such as an azide, an alkyne or a norbornene group. Also provided are modified peptidoglycans conjugated to a molecule of interest via a linker.

DEFINITIONS

Figure 1:
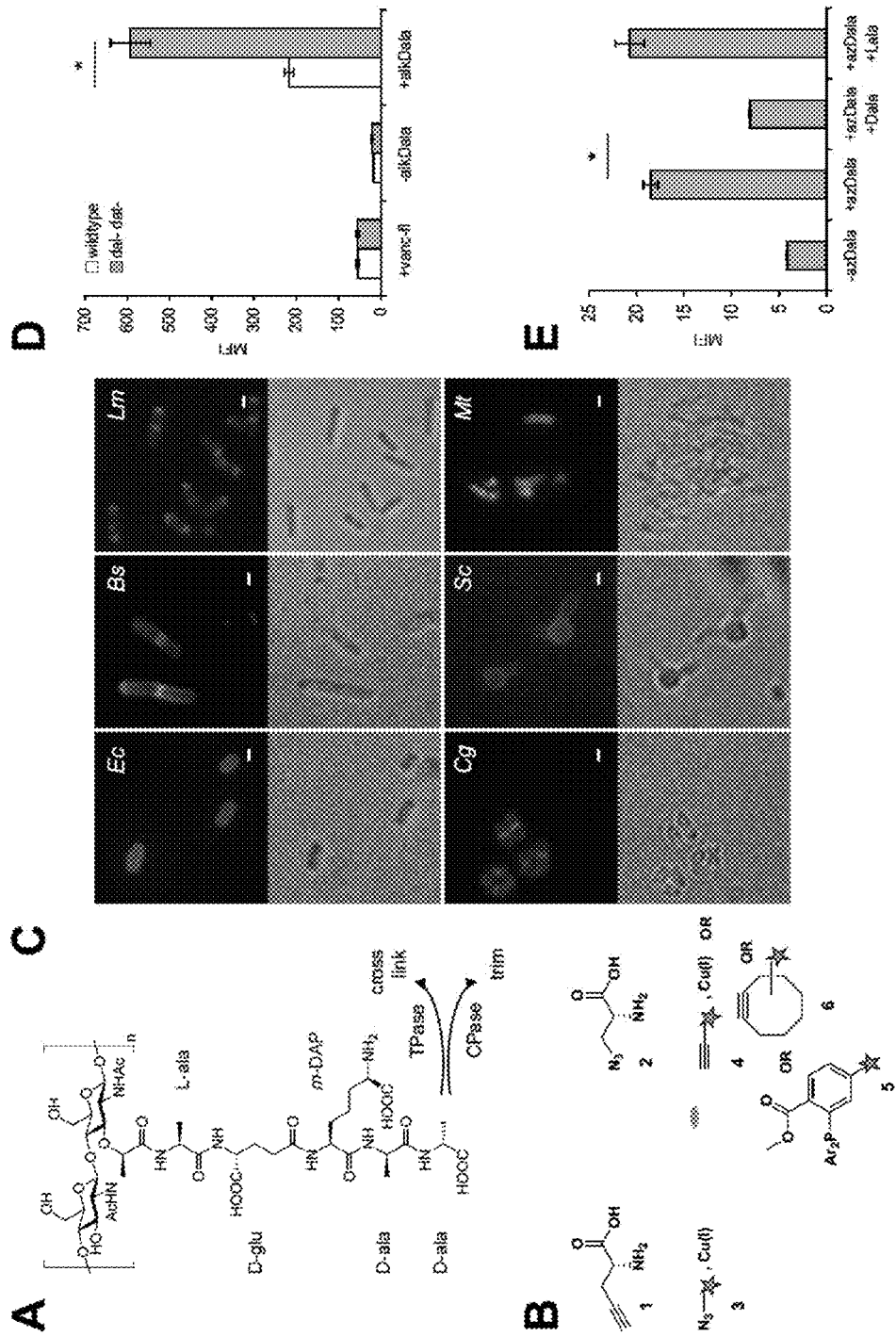
FIGS. 1A-E depict cell surface fluorescence resulting from incubation of bacteria in azido- and alkynyl-D-alanine analogs followed by reaction with click chemistry probes.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment or its synthetic environment and is at least 60% free, at least 75% free, at least 90% free, at least 95% free, at least 98% free, or at least 99% free from other components with which it is naturally associated, or is at least 60% free, at least 75% free, at least 90% free, at least 95% free, at least 98% free, or at least 99% free from contaminants associated with synthesis of the compound.

The term "aryl" as used herein means 5- and 6-membered single-aromatic radicals which may include from zero to four heteroatoms. Representative aryls include phenyl, thienyl, furanyl, pyridinyl, (is)oxazoyl and the like.

The term "lower alkyl", alone or in combination, generally means an acyclic alkyl radical containing from 1 to about 10, e.g., from 1 to about 8 carbon atoms, or from 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, iso-propyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, triflorom-ethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

The terms "halo" and "halogen" refer to the fluoro, chloro, bromo or iodo groups. There can be one or more halogen, which are the same or different.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl) hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl)ethyl, 4-(2',6'-dihydroxy phenyl)n-hexyl, 2-(5'-cyano-3'-methoxyphenyl) n-pentyl, 3-(2',6'-dimethylphenyl)n-propyl, 4-chloro-3-aminobenzyl, 6-(4'-methoxyphenyl)-3-carboxy(n-hexyl), 5-(4'-aminomethylphenyl)-3-(aminomethyl)n-pentyl, 5-phenyl-3-oxo-n-pent-1-yl, (4-hydroxynapth-2-yl)methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, e.g., to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature, or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers."

Isomers that differ in the arrangement of their atoms in space are termed "stereoisomers." Stereoisomers that are not minor images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)— or (S)— stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an alkyne-modified D-amino acid" includes a plurality of such amino acids and reference to "the azide-modified D-amino acid" includes reference to one or more azide-modified D-amino acids and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides modified bacteria and modified peptidoglycan comprising modified D-amino acids; compositions comprising the modified bacteria or peptidoglycan; and methods of using the modified bacteria or peptidoglycan.

Modified Peptidoglycan

The present disclosure provides modified peptidoglycan comprising modified D-amino acids. Modified D-amino acids allow labeling of peptidoglycan modified with a bioorthogonal functional group. Any convenient bioorthogonal functional groups may be utilized in the subject modified D-amino acids and modified peptidoglycans. Bioorthogonal functional groups of interest include, but are not limited to: azide, alkyne, alkene, norbornene, trans-cyclooctene and tetrazole. In some cases, the modified D-amino acids are azide-, alkyne-, or norbornene-modified D-amino acids.

As shown schematically in FIG. 1A, peptidoglycan (PG) is a polymer comprising sugars and amino acids. The sugar component consists of alternating residues of β-(1,4) linked N-acetylglucosamine (GlcNAc) and N-acetylmuramic acid (MurNAc). Attached to the MurNAc is a peptide chain of three to five amino acids. In some cases, a subject modified PG comprises a peptide chain of four amino acids. In some instances, a subject modified PG comprises a peptide chain of five amino acids.

A subject modified PG comprises a peptide chain of three to five amino acids, wherein at least one of the amino acids is a modified D-amino acid, and wherein the peptide chain is linked to a MurNAc moiety in the PG polymer. In some instances, the at least one modified D-amino acid is located at one or more of positions 2, 4, and 5. In some embodiments, only one amino acid of the peptide chain is modified D-amino acid, such as an azide-, alkyne-, or norbornene-modified D-amino acid. In some cases, a subject modified PG comprises an azide-, alkyne-, or norbornene-modified D-amino acid in position 2, i.e., the second amino acid from the MurNAc moiety. In other cases, a subject modified PG comprises an azide-, alkyne-, or norbornene-modified D-amino acid in position 4, i.e., the fourth amino acid from the MurNAc moiety. In other cases, a subject modified PG comprises an azide-, alkyne-, or norbornene-modified D-amino acid in position 5, i.e., the fifth amino acid from the MurNAc moiety.

D-amino acids that can be modified to produce a modified D-amino acid include any genetically encoded or non-encoded amino acid. In some embodiments, a modified D-amino acid is any one of the twenty encoded amino acids. In some embodiments, a modified D-amino acid, such as an azide-modified, norbornene-modified or alkyne-modified D-amino acid, suitable for incorporation into PG to generate a modified PG is a non-canonical D-amino acid. In some embodiments, a modified D-amino acid, such as an azide-modified, norbornene-modified or alkyne-modified D-amino acid, suitable for incorporation into PG to generate a modified PG is D-alanine. Diverse bacterial phyla produce and incorporate D-amino acids other than D-alanine into PG. See, e.g., Lam et al. (2009) *Science* 325:1552; and Cava et al. (2011) *EMBO J.* 30:3442. Thus, in some embodiments, a modified D-amino acid suitable for incorporation into PG to generate a modified PG is derived from D-methionine, D-leucine, D-tyrosine, D-phenylalanine, D-cysteine, or D-threonine, or D-isoleucine.

In some cases, a modified PG can comprise an azide-modified, a norbornene-modified or an alkyne-modified D-amino acid, where the modified amino acid is a non-encoded amino acid.

In some embodiments, the modified D-amino acid is described by formula XXXI:

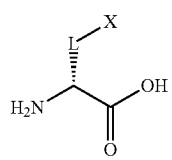

(Formula XXXI)

where L is an optional linker; and X is an azide, a norbornene, a tetrazole or an alkyne.

In some embodiments, the modified D-amino acid is described by formula XXXII:

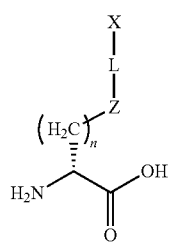

Formula (XXXII)

where n is 0 or an integer from 1 to 12; Z is a linking functional group; L is an optional linker; and X is an azide, a norbornene, a tetrazole or an alkyne.

In certain embodiments of Formula (XXXII), n is 1, 2, 3, 4, 5 or 6. In certain embodiments of Formula (XXXII), n is 1. In certain embodiments of Formula (XXXII), n is 2. In certain embodiments of Formula (XXXII), n is 3. In certain embodiments of Formula (XXXII), n is 4. In certain embodiments of Formula (XXXII), n is 5. In certain embodiments of Formula (XXXII), n is 6. In certain embodiments of Formula (XXXII), n is 0.

Any convenient linking functional groups may be utilized in the subject modified D-amino acids. Z may be utilized in any convenient configuration as a linking functional group to connect the D-amino acid to the X group. In certain embodiments of Formula (XXXII), Z is selected from an amido, a urethane, an ester, an ether, a thioether, a sulfonamide, a keto and an amino. In certain embodiments of Formula (XXXII), Z is —NHC(O)—. In certain embodiments of Formula (XXXII), Z is —NHC(O)O—. In certain embodiments of Formula (XXXII), Z is —OCO—. In certain embodiments of Formula (XXXII), Z is —O—. In certain embodiments of Formula (XXXII), Z is absent.

Any convenient linkers may be utilized in the subject modified D-amino acids. In certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxy-polyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Other linkers are also possible, as shown in the modified D-amino acids and reagents described in more detail below.

Any convenient X groups may be utilized in the subject D-modified amino acids. X may be connected to the amino acid via optional linker L via any convenient configuration and at any convenient position of X. In certain embodiments of Formula (XXXII), X is an azide-containing group. In certain embodiments of Formula (XXXII), X is —N$_3$.

In certain embodiments of Formula (XXXII), X is norbornene.

In certain embodiments of Formula (XXXII), X is tetrazole.

In certain embodiments of Formula (XXXII), X is an alkyne. In certain embodiments of Formula (XXXII), X is a propargyl group.

In certain embodiments of Formula (XXXII), X is a cyclooctyne. Any convenient cyclooctyne groups may be utilized in the subject D-amino acids. Cyclooctyne groups of interest which may be adapted for use in the subject modified D-amino acids include, but are not limited to, one of the cyclooctyne groups described in the azide-reactive reagents herein. In certain embodiments, the modified D-amino acid includes a cyclooctyne groups (e.g., X) as described in one of Formulae I to XXVI herein.

In certain embodiments of Formula (XXXII), X is described by the following structure:

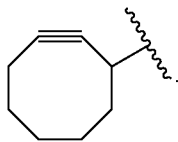 [SMILES: *C1C#CCCCCC1]

In certain embodiments of Formula (XXXII), X is described by the following structure:

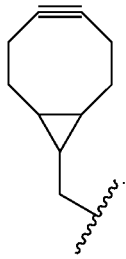

In certain embodiments of Formula (XXXII), X is described by one of the following structures:

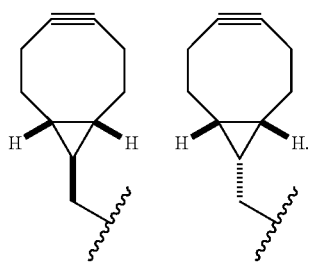

In certain embodiments of Formula (XXXII), Z is —NHC(O)O— and X-L is selected from one of the following:

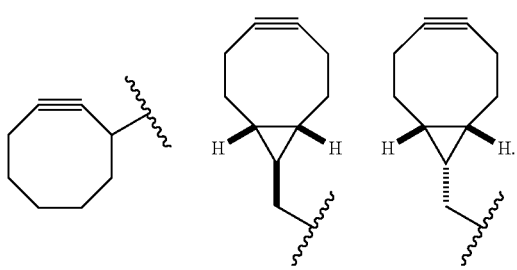

In certain embodiments, n is 1. In certain embodiments, n is 4.

In certain embodiments, the modified D-amino acid is R-2-amino-3-azidopropanoic acid or propargylglycine. In some embodiments, the modified D-amino acid is described by one of the following:

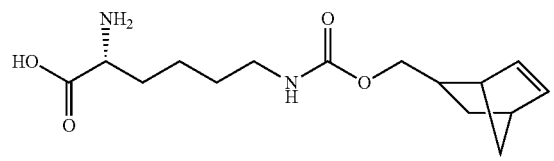

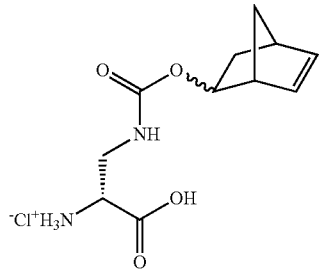

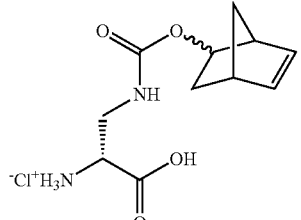

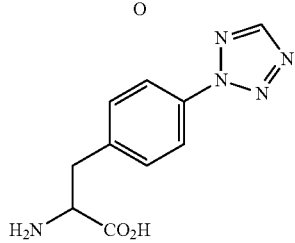

Analogs of such peptides include those containing residues other than naturally occurring L-amino acids, e.g., D-amino acids or non-naturally occurring synthetic amino acids (e.g., non-natural, non-encoded amino acids).

The following are non-limiting examples of amino acid modifications (e.g., modifications to introduce a bioorthogonal functional group such as an azide, an alkyne, a norbornene, a trans-cyclooctene, or a tetrazole) that can be made:

a) substitution of alkyl-substituted hydrophobic amino acids: including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions;

b) substitution of aromatic-substituted hydrophobic amino acids: including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains: including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma,gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid;

d) substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids;

e) substitution of side chain amide residues: including asparagine, glutamine, and alkyl or aromatic substituted derivatives of asparagine or glutamine; and f) substitution of hydroxyl containing amino acids: including serine, threonine, homoserine, 2,3-diaminopropionic acid, and alkyl or aromatic substituted derivatives of serine or threonine.

In some cases, a subject modified PG comprises one or more naturally occurring non-genetically encoded L-amino acids, synthetic L-amino acids or D-enantiomers of an amino acid. A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof.

Reagents

The modified PG or modified D-amino acid may be conjugated to any convenient reagent, such as a reagent that includes a detectable label. The reagent may include a compatible functional group that is capable of conjugating to the modified PG, e.g., via bioorthogonal conjugation with the bioorthogonal functional group (e.g., an azide, a norbornene or alkyne group) of a modified PG. A variety of bioorthogonal chemistries and reagents may be utilized in the subject modified PGs, D-amino acids and conjugation reagents, including but not limited to, Click chemistry groups and reagents (e.g., as described by Sharpless et al., (2001), "Click Chemistry: Diverse Chemical Function from a Few Good Reactions", Angewandte Chemie International Edition 40 (11): 2004-2021), photoinduced cycloaddition chemistry groups and reagents (e.g., photo-click chemistry and groups, as described by Lin et al., "Photoinducible Bioorthogonal Chemistry: A Spatiotemporally Controllable Tool to Visualize and Perturb Proteins in Live Cells", ACCOUNTS OF CHEMICAL RESEARCH '828-839' 2011 'Vol. 44, No. 9); norbornene-tetrazine chemistry groups and reagents (e.g., as described by Carell et al. "A Genetically Encoded Norbornene Amino Acid for the Mild and Selective Modification of Proteins in a Copper-Free Click Reaction", Angew. Chem. Int. Ed. 1012, 51, 4466-4469); Staudinger ligation groups and reagents (e.g., as described by Bertozzi et al., (2000), "Cell Surface Engineering by a Modified Staudinger Reaction", Science 287 (5460): 2007) (e.g., using azido and phosphine groups), and other bioconjugation groups and reagents (e.g., as described by Hermanson, Bioconjugate Techniques, Second Edition, Academic Press, 2008). In certain embodiments, the reagent includes a compatible functional group selected from an azido, a phosphine (e.g., a triaryl phosphine or a trialkyl phosphine or mixtures thereof), a dithiol, an active ester, an alkynyl, an alkenyl, a tetrazine, a tetrazole, a hydrazoyl chloride, and a norbornenyl.

Reagents reactive with azide-modified D-amino acids

Any convenient azide-reactive reagents may be utilized for conjugation to the subject azide-modified PGs and D-amino acids. Reagents reactive with azide-modified amino acids include, but are not limited to, reagents that include an alkyne functional group, such as click chemistry or copper-free click chemistry reagents.

Alkynyl reagents

Any convenient alkynyl groups and chemistries may be adapted for use in the subject azido-reactive reagents. Alkynyl groups and chemistries of interest include, but are not limited to: the cycloalkyne and heterocycloalkyne groups described by Bertozzi et al. in U.S. patent application Ser. No. 12/049,034, filed Mar. 14, 2008; the modified cycloalkyne groups described by Jewett et al. in U.S. patent application Ser. No. 13/024,908, filed Feb. 10, 2011; the fused cyclooctyne compounds described by Van Delft et al. in WO/2011/136645, which applications are incorporated herein by reference in their entirety.

In some embodiments, the alkynyl reagent is a compound of the formula:

X-L-Y, wherein:

X is an alkyne group, optionally substituted with Y, and in some embodiments one or more additional groups; L is a linker; and Y is a molecule of interest, e.g., a detectable label.

In some cases, L is $(T)_n$, where each T is a divalent moiety independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine; and each n is a number selected from zero to 40.

In some embodiments, Y is a molecule of interest, where suitable molecules of interest include, but are not limited to, a detectable label; a toxin (including cytotoxins); a peptide; a drug; a member of a specific binding pair; an epitope tag; a strained azacycloalkynone group; and the like.

In some embodiments, X is a cycloalkyne group (e.g., a cyclooctyne group) or a heterocycloalkyne group.

In some embodiments, the alkynyl reagent is described by Formula I:

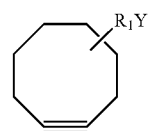

Formula I where:

Y is a molecule of interest; and $R_1$ is a linker (e.g., as described herein) that includes one or more of the following groups: carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro. $R_1$ can be at any position on the cyclooctyne group other than at the two carbons joined by the triple bond.

In some instances, a cyclooctyne compound that may be adapted for use in the subject alkynyl reagents, is described by:

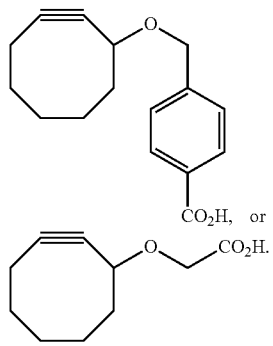

In some embodiments, the alkynyl reagent is of Formula I, wherein one or more of the carbon atoms in the cyclooctyne ring, other than the two carbon atoms joined by a triple bond, is substituted with one or more electron-withdrawing groups, e.g., a halo (bromo, chloro, fluoro, iodo), a nitro group, a cyano group, a sulfone group, or a sulfonic acid group. Thus, e.g., in some embodiments, a subject alkynyl reagent is of Formula II:

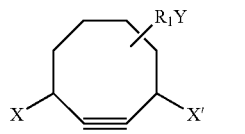

Formula II where: each of X and X' is independently:

(a) H;

(b) one or two halogen atoms (e.g., bromo, chloro, fluoro, iodo);

(c) —W—$(CH_2)_n$—Z (where: n is an integer from 1-4 (e.g., n=1, 2, 3, or 4); W, if present, is O, N, or S; and Z is nitro, cyano, sulfonic acid, or a halogen);

(d) —$(CH_2)_n$—W—$(CH_2)_m$—Z (where: n and m are each independently 1 or 2; W is O, N, S, or sulfonyl; if W is O, N, or S, then Z is nitro, cyano, or halogen; and if W is sulfonyl, then Z is H); or (e) —$(CH_2)_n$—Z (where: n is an integer from 1-4 (e.g., n=1, 2, 3, or 4); and Z is nitro, cyano, sulfonic acid, or a halogen);

Y is a molecule of interest; and $R_1$ is a linker that includes one or more of the following groups: carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro. $R_1$ can be at any position on the cyclooctyne group other than at the two carbons linked by the triple bond.

In some instances, a cyclooctyne compound that may be adapted for use in the subject alkynyl reagents, is described by:

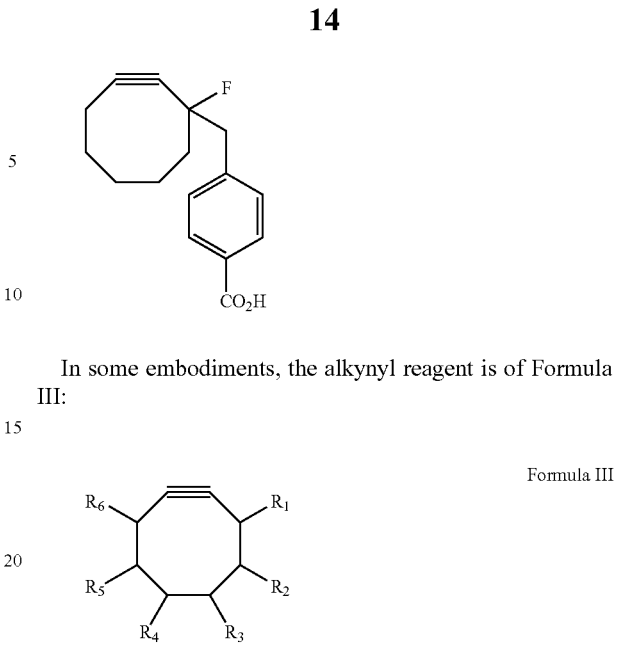

In some embodiments, the alkynyl reagent is of Formula III:

Formula III wherein each of $R_1$-$R_6$ is independently H; one or two halogen atoms (e.g., bromo, chloro, fluoro, iodo); a carboxylic acid; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; a nitro; —W—$(CH_2)_n$—Z (where: n is an integer from 1-4 (e.g., n=1, 2, 3, or 4), wherein W, if present, is O, N, or S; and Z is nitro, cyano, sulfonic acid, or a halogen); —$(CH_2)_n$—W—$(CH_2)_m$—Z (where: n and m are each independently 1 or 2; W is O, N, S, or sulfonyl, wherein if W is O, N, or S, then Z is nitro, cyano, or halogen, and wherein and if W is sulfonyl, then Z is H); or —$(CH_2)_n$—Z (where: n is an integer from 1-4 (e.g., n=1, 2, 3, or 4), and wherein Z is nitro, cyano, sulfonic acid, or a halogen);

wherein $R_3$ is optionally linked to $R_4$ through Y thus forming a substituted or unsubstituted cycloalkyl or substituted or unsubstituted heterocycloalkyl substituient on the cycloalkyne ring, wherein Y, if present, is C, O, N, or S; and wherein each of $R_1$-$R_6$ is optionally independently linked to a moiety that comprises a reactive group that facilitates covalent attachment of a molecule of interest; or a molecule of interest.

In some embodiments of Formula III, $R_1$ is two fluoride atoms, one or more of $R_2$, $R_3$, $R_4$, and $R_5$ is a fluorophore, and $R_6$ is —$OR_7$, where —$OR_7$ is a leaving group with a quencher (e.g., and ester, a sulfonate, etc.).

In some instances, a cyclooctyne compound that may be adapted for use in the subject alkynyl reagents, is described by:

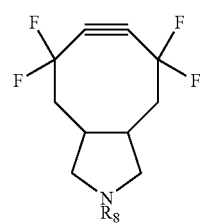

where $R_8$ is selected from H; a halogen atom (e.g., bromo, fluoro, chloro, iodo); an aliphatic group, a substituted or unsubstituted alkyl group; an alkenyl group; an alkynyl group; a carboxylic acid, an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; and a nitro.

In some embodiments, the alkynyl reagent is of Formula IV:

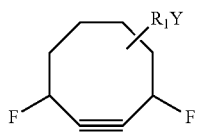

Formula IV where:

Y is a molecule of interest; and $R_1$ is a linker that includes one or more of the following groups: a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro. $R_1$ can be at any position on the cyclooctyne group other than at the two carbons linked by the triple bond.

In some instances, a cyclooctyne compound that may be adapted for use in the subject alkynyl reagents, is described by:

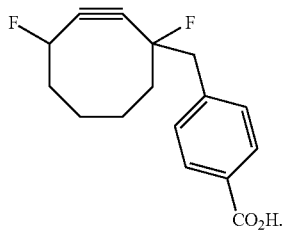 [SMILES: O=C(O)c1ccc(CC2(F)C#CC(F)CCCC2)cc1]

In some embodiments, the alkynyl reagent is of Formula V:

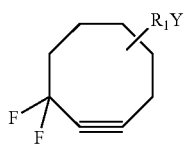

Formula V where:

Y is a molecule of interest; and $R_1$ is a linker that includes one or more of the following groups: carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro. $R_1$ can be at any position on the cyclooctyne group other than at the two carbons linked by the triple bond, and other than the fluoride-substituted carbon.

In some instances, a cyclooctyne compound that may be adapted for use in the subject alkynyl reagents, is described by one of the following:

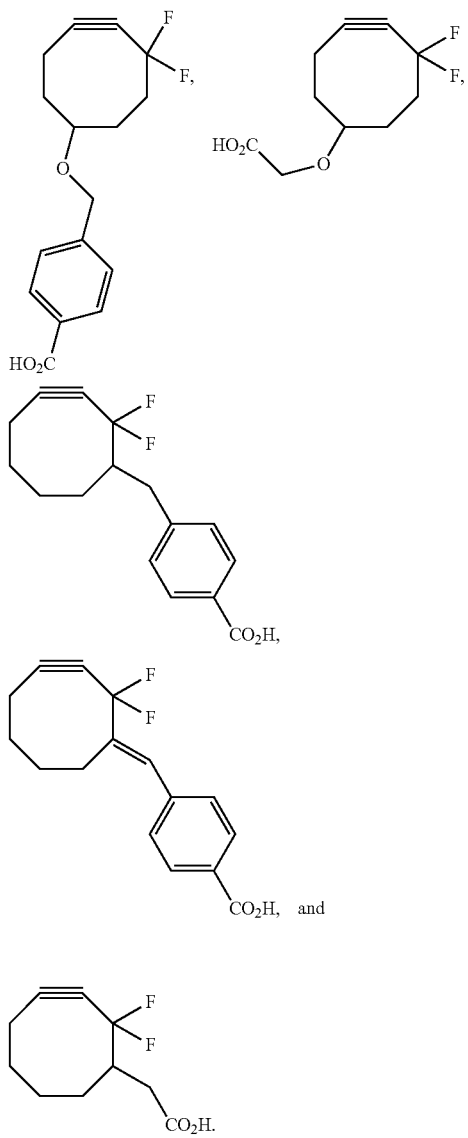

In some embodiments, the alkynyl reagent is of Formula VI:

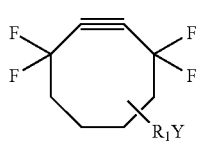

Formula VI where Y is a molecule of interest; and $R_1$ is a linker that includes one or more of the following groups: a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro. $R_1$ can be at any position on the cyclooctyne group other than at the two carbons linked by the triple bond, and other than the fluoride-substituted carbons.

In some embodiments, the alkynyl reagent is of Formula VII:

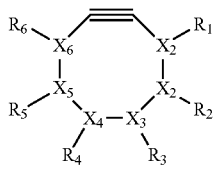

Formula VII wherein five of $X_1$-$X_6$ are carbon;

wherein one of $X_1$-$X_6$ is N, O, P, or S;

wherein each of $R_1$-$R_6$ is independently H; one or two halogen atoms (e.g., bromo, chloro, fluoro, iodo); a carboxylic acid; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; a nitro; —W—$(CH_2)_n$—Z (where: n is an integer from 1-4 (e.g., n=1, 2, 3, or 4), wherein W, if present, is O, N, or S; and Z is nitro, cyano, sulfonic acid, or a halogen); —$(CH_2)_n$—W—$(CH_2)_m$—Z (where: n and m are each independently 1 or 2; W is O, N, S, or sulfonyl, wherein if W is O, N, or S, then Z is nitro, cyano, or halogen, and wherein and if W is sulfonyl, then Z is H); or —$(CH_2)_n$—Z (where: n is an integer from 1-4 (e.g., n=1, 2, 3, or 4), and wherein Z is nitro, cyano, sulfonic acid, or a halogen); and wherein each of $R_1$-$R_6$ is optionally independently linked to a molecule of interest.

In some embodiments, a cycloctyne compound that may be adapted for use in the alkynyl reagent is described by one of Formulas VIII and IX:

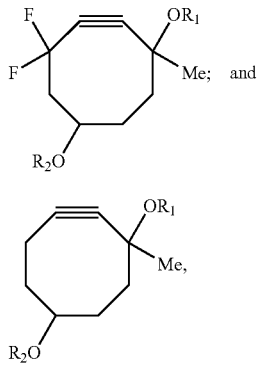

Formula VIII

Formula IX where each —OR is independently a leaving group.

In some embodiments, a subject modified cycloalkyne is a heteroalkyne of Formula X:

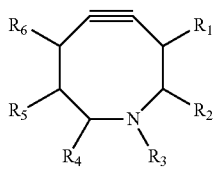

Formula X wherein each of $R_1$-$R_6$ is independently H; one or two halogen atoms (e.g., bromo, chloro, fluoro, iodo); a carboxylic acid; a methoxy group; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; a nitro; —W—$(CH_2)_n$—Z (where: n is an integer from 1-4 (e.g., n=1, 2, 3, or 4), wherein W, if present, is O, N, or S; and Z is nitro, cyano, sulfonic acid, or a halogen); —$(CH_2)_n$—W—$(CH_2)_m$—Z (where: n and m are each independently 1 or 2; W is O, N, S, or sulfonyl, wherein if W is O, N, or S, then Z is nitro, cyano, or halogen, and wherein and if W is sulfonyl, then Z is H); or —$(CH_2)_n$—Z (where: n is an integer from 1-4 (e.g., n=1, 2, 3, or 4), and wherein Z is nitro, cyano, sulfonic acid, or a halogen); and wherein each of $R_1$-$R_6$ is optionally independently linked to a molecule of interest.

In some instances, a cyclooctyne compound that may be adapted for use in the subject alkynyl reagents, is described by one of the following:

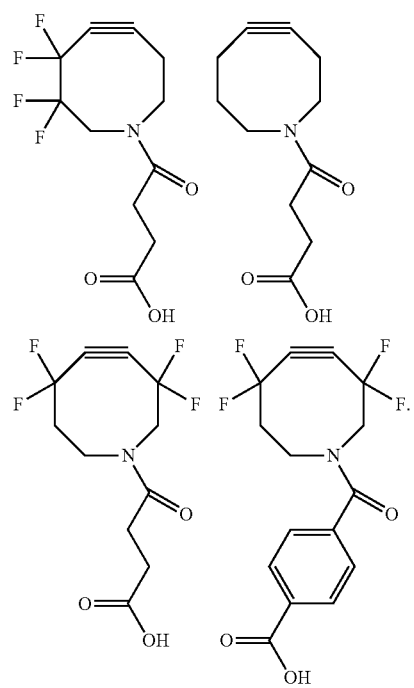

In some embodiments, the alkynyl reagent has the structure of one of Formulas XI-XVI:

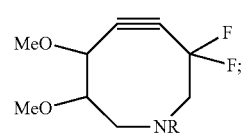

Formula XI

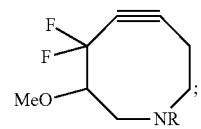

Formula XII

-continued

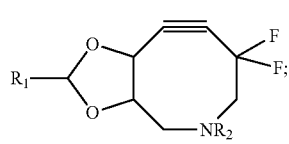
Formula XIII

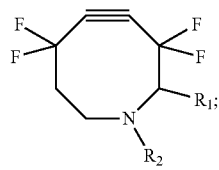
Formula XIV

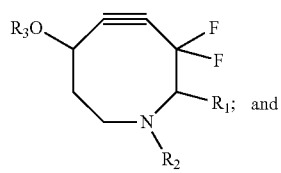
Formula XV

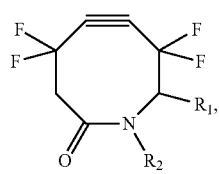
Formula XVI where R, $R_1$, $R_2$, and $R_3$ are each independently H; one or two halogen atoms (e.g., bromo, chloro, fluoro, iodo); a carboxylic acid; a methoxy group; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; or a nitro;

wherein —OR is in some embodiments a leaving group with a quencher; and wherein each R is optionally independently linked to a molecule of interest.

In some embodiments, the alkynyl reagent has the structure of Formula XVII:

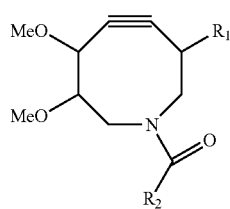
Formula XVII where $R_1$ and $R_2$ are each independently H; one or two halogen atoms (e.g., bromo, chloro, fluoro, iodo); a carboxylic acid; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; or a nitro; and wherein each of $R_1$ and $R_2$ is optionally independently linked to a moiety that comprises a reactive group that facilitates covalent attachment of a molecule of interest; or a molecule of interest.

In some instances, a cyclooctyne compound that may be adapted for use in the subject alkynyl reagents, is described by:

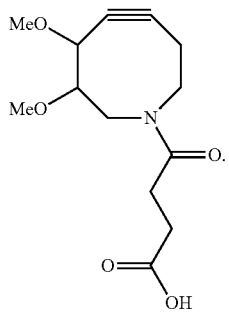 [SMILES: COC1C#CCCN(C(=O)CCC(=O)O)CC1OC]

In some embodiments, the alkynyl reagent has the structure of Formula XVIII:

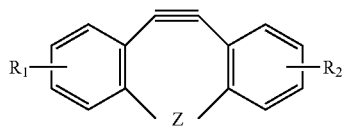
Formula XVIII where Z is —$CH_2$—$CH_2$—, —CH=CH—, —Se(O)O—, —C(O)O—, —C($R_3$)($R_4$)O—, —N($R_5$)N($R_6$)—, —CH(O$R_7$)$CH_2$—, or —S(O)O—;

where $R_1$ and $R_2$ are each independently H; one or two halogen atoms (e.g., bromo, chloro, fluoro, iodo); a carboxylic acid; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; or a nitro;

where $R_3$ to $R_7$ is each independently selected from H; a halogen atom (e.g., bromo, fluoro, chloro, iodo); an aliphatic group, a substituted or unsubstituted alkyl group; an alkenyl group; an alkynyl group; a carboxylic acid, an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; or a nitro; and wherein each of $R_1$ and $R_2$ is optionally independently linked to a molecule of interest.

In some embodiments, the alkynyl reagent is described by the structure of one of Formulas XIX, XX, and XXI:

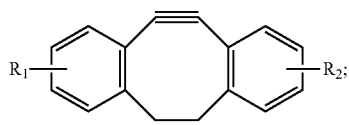
Formula XIX

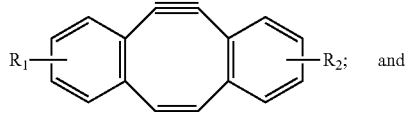
Formula XX
and

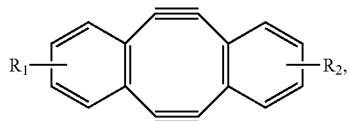
Formula XXI where $R_1$ and $R_2$ are as defined above for Formula XVIII.

In some embodiments, the alkynyl reagent is described by the structure of Formula XXIb:

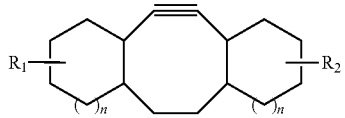

Formula XXIb wherein R1 and R2 are each independently H; one or two halogen atoms (e.g., bromo, chloro, fluoro, iodo); a carboxylic acid; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; or a nitro;

wherein each n is independently 0, 1, or 2; and wherein each of $R_1$ and $R_2$ is optionally independently linked to a molecule of interest.

In some embodiments, the alkynyl reagent is of Formula XXIII:

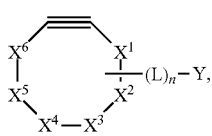

Formula XXII wherein five of $X^1$-$X^6$ are carbons, where $X^1$-$X^6$ may be saturated or unsaturated, substituted or unsubstituted;

one of $X^1$-$X^6$ is nitrogen;

the $X^1$-$X^6$ that is vicinal to the $X^1$-$X^6$ that is nitrogen is C=O;

at least two of $X^1$-$X^6$ are sp$^2$ centers vicinal to each other;

each L is a divalent moiety independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;

each n is a number selected from zero to 40; and

Y is a molecule of interest.

In some embodiments, in Formula XXII, one of $X^2$-$X^5$ is nitrogen. In some embodiments, in Formula XXII, one of $X^3$ and $X^4$ is nitrogen. In certain embodiments, two of $X^1$-$X^6$ are cyclically linked to form a fused aryl ring. In certain cases, $X^5$ and $X^6$ are part of a fused phenyl ring, and/or $X^1$ and $X^2$ are part of a fused phenyl ring In some embodiments, in Formula XXII, at least four of $X^1$-$X^6$ are sp$^2$ centers vicinal to each other. In some embodiments, in Formula XXII, $X^1$ and $X^2$ are sp$^2$ centers vicinal to each other. In some embodiments, in Formula XXII, $X^5$ and $X^6$ are sp$^2$ centers vicinal to each other. In some embodiments, in Formula XXII, $X^2$ and $X^3$ are sp$^2$ centers vicinal to each other.

In some embodiments, in Formula XXII, at least one of $X^1$-$X^2$ is the carbon of a carbonyl group. In some embodiments, in Formula XXII, at least one of $X^3$ and $X^4$ is the carbon of a carbonyl group. In some embodiments, in Formula XXII, at least one of $X^4$ and $X^5$ is the carbon of a carbonyl group. In some embodiments, the carbonyl group is the carbonyl of an amido group. In some embodiments, the carbonyl group is the carbonyl of an urea group.

In some embodiments, the alkynyl reagent is of Formula XXIII:

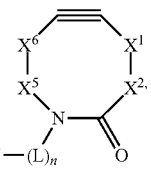

Formula XXIII wherein at least two of $X^1$, $X^2$, $X^5$, and $X^6$ are sp$^2$ centers vicinal to each other (e.g., $X^1$ and $X^2$, and/or $X^5$ and $X^6$), where $X^1$ and $X^2$, may be cyclically linked (e.g., to form a fused a phenyl ring) and $X^5$ and $X^6$, may be cyclically linked (e.g., to form a fused a phenyl ring);

each L is a divalent moiety independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;

n is an integer selected from zero to 40; and

Y is a molecule of interest.

In some embodiments, the alkynyl reagent is of Formula XXIV:

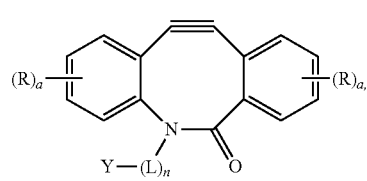

Formula XXIV wherein

L is a divalent moiety selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;

n is an integer selected from zero to 40;

each R is independently selected from alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, thioketo, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl;

each a is an integer selected from zero to four; and

Y is a molecule of interest.

In Formula XXIV, the —(R)a may represent one or more optional aryl substituents (e.g., 1, 2, 3 or 4 aryl substituents), each R group independently attached to any suitable carbon of the aryl ring.

In some embodiments, the alkynyl reagent is of Formula XXV:

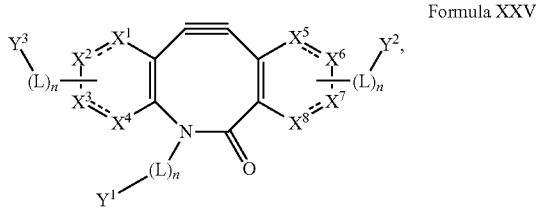

Formula XXV where $X^1$-$X^8$ are each independently selected from carbon (e.g., CH or CR), nitrogen and silicon (e.g., Si—R);

each L is a divalent moiety selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine number independently selected from zero to 40;

each R is independently selected from alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, thioketo, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; and $Y^1$—$Y^3$ are each independently selected from H and a molecule of interest.

In some embodiments, the alkynyl reagent is of Formula XXVI:

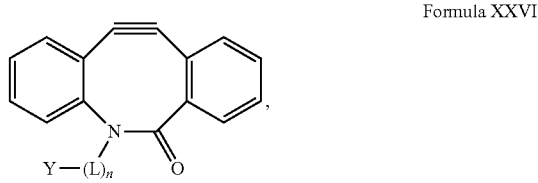

Formula XXVI wherein

L is a divalent moiety selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;

n is an integer selected from zero to 40; and

Y is a molecule of interest.

In some embodiments, the alkynyl reagent, or a precursor thereof, is described by the structure of one of the following:

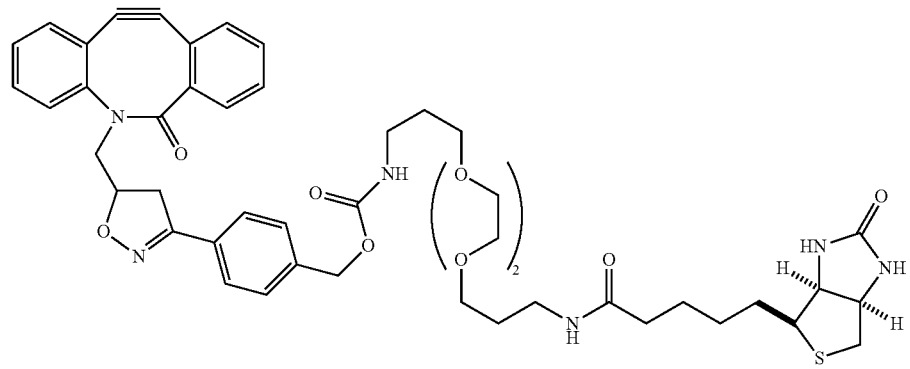

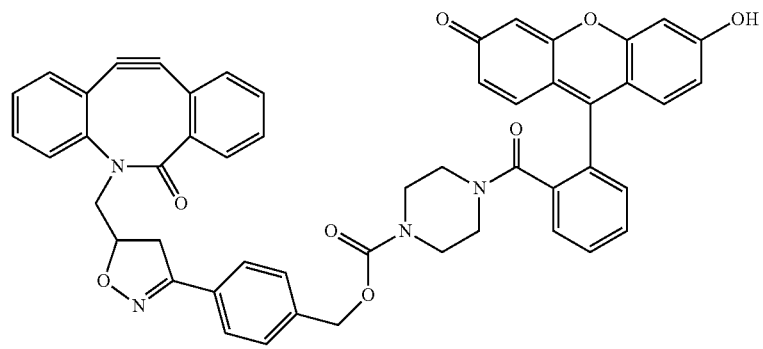

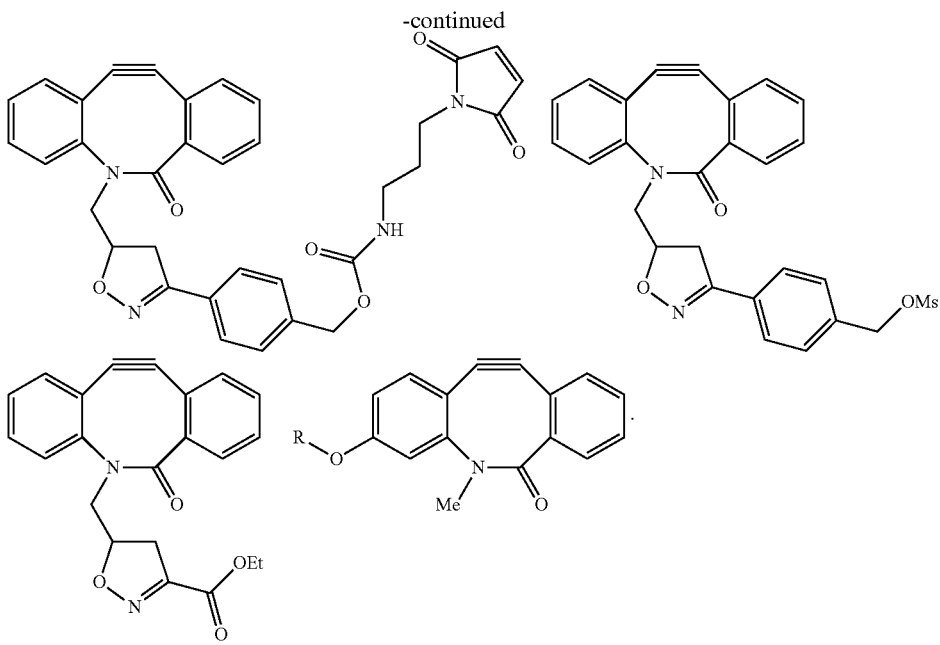

wherein R is selected from hydrogen, alkyl, sulfate, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl, sulfonyl, sulfonamide, sulfonyl ester, amino, and substituted amino;

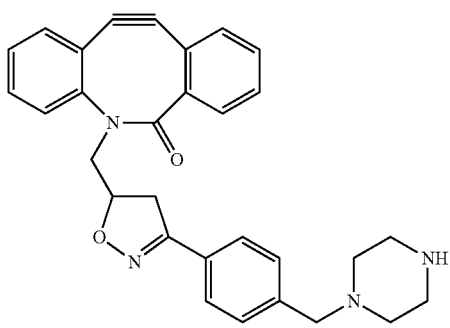

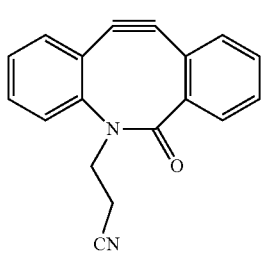

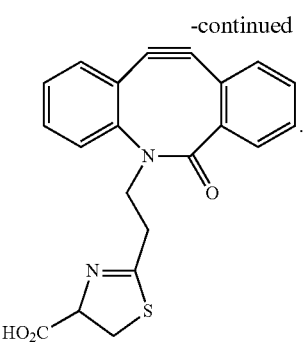

A subject alkynyl reagent may be prepared using any convenient method, including but not limited to coupling a molecule of interest to a cyclooctyne group (e.g., as described herein) using any suitable method and chemistry. For example, coupling can be achieved using a metal-catalyzed cross-coupling or metal-halogen exchange/nucleophilic attack method, as illustrated in the following scheme:

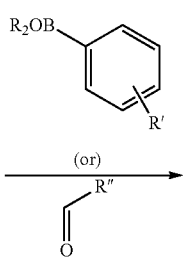

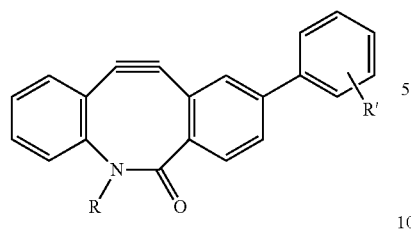

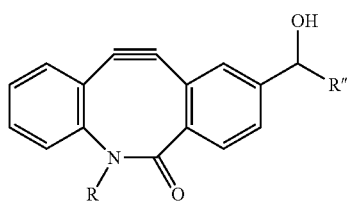

where R' and R" are molecules of interest, and each R is independently an alkyl, a substituted alkyl, an aryl or a substituted aryl, and where optionally the R groups of the boronic ester may be cyclically linked.

In some instances, the alkynyl reagent is a DIBO, DIBAC or BARAC reagent, or derivative thereof. In certain cases, the alkynyl reagent is a DIBO, DIBAC or BARAC reagent described by one of the following:

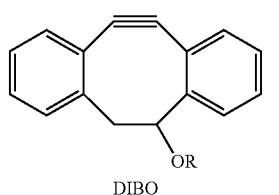
DIBO

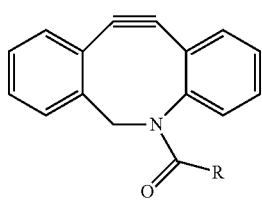
DIBAC

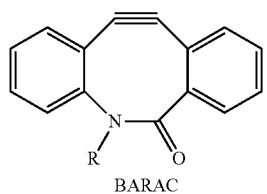
BARAC where R includes a molecule of interest (e.g., a detectable label), connected to the cyclooctyne group via an optional linker.

In some embodiments, the alkynyl reagent is described by one of the following:

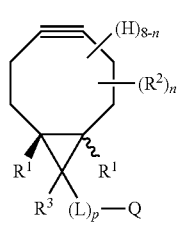
(XXVII)

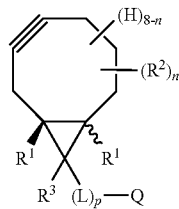
(XXVIII)

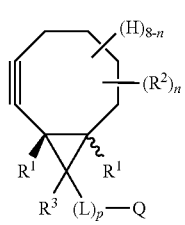
(XXIX)

wherein: n is 0 to 8; p is 0 or 1;

R3 is selected from the group consisting of [(L)p-Q], hydrogen, halogen, C1-groups, C6-C24 (hetero)aryl groups, C7-C24 alkyl(hetero)aryl groups and C7-C24 (hetero)arylalkyl groups, the alkyl groups optionally being interrupted by one or more hetero-atoms selected from the group consisting of O, N and S, wherein the alkyl groups, (hetero)aryl groups, alkyl(hetero)aryl groups and (hetero)arylalkyl groups are independently optionally substituted with one or more substituents independently selected from the group consisting of C1-C12 alkyl groups, C2-C12 alkenyl groups, C2-C12 alkynyl groups, C3-C12 cycloalkyl groups, C1-C12 alkoxy groups, $C2-C_{12}$ alkenyloxy groups, C2-C12 alkynyloxy groups, C3-C12 cycloalkyloxy groups, halogens, amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S, wherein the silyl groups are represented by the formula $(R4)_3Si—$, wherein R4 is independently selected from the group consisting of C1-C12 alkyl groups, C2-alkenyl groups, C2-C12 alkynyl groups, C3-C12 cycloalkyl groups, C1-C12 alkoxy groups, $C2-C_{1-2}$ alkenyloxy groups, C2-C12 alkynyloxy groups and C3-C12 cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S;

L is a linking group selected from linear or branched $C1-C_{24}$ alkylene groups, C24 alkenylene groups, C2-C24 alkynylene groups, C3-C24 cycloalkylene groups, C5-C24 cycloalkenylene groups, C8-C24 cycloalkynylene groups, C7-C24 alkyl(hetero)arylene groups, C7-C24 (hetero)arylalkylene groups, C8-C24 (hetero)arylalkenylene groups, C9-C24 (hetero)arylalkynylene groups, the alkylene groups, alkenylene groups, alkynylene groups, cycloalkylene groups, cycloalkenylene groups, cycloalkynylene groups, alkyl(hetero)arylene groups, (hetero)arylalkylene groups, (hetero)arylalkenylene groups and (hetero)arylalkynylene groups optionally being substituted with one or more substituents independently selected from the group consisting of C1-C12 alkyl groups, C2-C12 alkenyl groups, C2-C12 alkynyl groups, C3-C12 cycloalkyl groups, C5-C12 cycloalkenyl groups, C8-C12 cycloalkynyl groups, C1-C12 alkoxy groups, C2-C12 alkenyloxy groups, C2-C12 alkynyloxy groups, C3-C12 cycloalkyloxy groups, halogens, amino groups, oxo and silyl groups, wherein the silyl groups can be represented by the formula (R4)$_3$Si—, wherein R4 is defined as above;

Q is a molecule of interest or a functional group selected from the group consisting of hydrogen, halogen, R6, —CH═C(R6)$_2$, —C≡CR6, —[C(R6)$_2$O]$_q$—R6, wherein q is in the range of 1 to 200, —CN, —N3, —NCX, —XCN, —XR6, —N(R6)2, —$^+$N(R6)$_3$, —C(X)N(R6)$_2$, —C(R6)$_2$XR6, —C(X)R6, —C(X)XR6, —S(0)R6, —S(0)$_2$R6, —S(0)OR6, —S(0)$_2$OR6, —S(0)N(R6)$_2$, —S(0)$_2$N(R6)$_2$, —OS(0)R6, —OS(0)$_2$R6, —OS(0)OR6, —OS(0)$_2$OR6, —P(0)(R6)(OR6), —P(0)(OR6)$_2$, —OP(0)(OR6)$_2$, —Si(R6)$_3$, —XC(X)R6, —XC(X)XR6, —XC(X)N(R6)$_2$, —N(R6)C(X)R6, —N(R6)C(X)XR6 and —N(R6)C(X)N(R6)$_2$, wherein X is oxygen or sulfur and wherein R6 is independently selected from the group consisting of hydrogen, halogen, C1-C$_{24}$ alkyl groups, C6-C24 (hetero)aryl groups, C7-C24 alkyl(hetero)aryl groups and C7-C24 (hetero)arylalkyl groups;

R1 is a molecule of interest or is independently selected from the group consisting of hydrogen, C1-C$_{24}$ alkyl groups, C6-C24 (hetero)aryl groups, C7-C24 alkyl(hetero)aryl groups and C7-C24 (hetero)arylalkyl groups; and R2 is a molecule of interest or is independently selected from the group consisting of halogen, —OR6, —NO$_2$, —CN, —S(O)$_2$R6, C1-C12 alkyl groups, C1-C12 aryl groups, C1-C12 alkylaryl groups and C1-C12 arylalkyl groups, wherein R6 is as defined above, and wherein the alkyl groups, aryl groups, alkylaryl groups and arylalkyl groups are optionally substituted.

Phosphine reagents

In some cases, the azide-reactive reagent includes a phosphine functional group. Without wishing to be bound by theory, reaction of the azido group with a phosphine reagent may lead to an iminophosphorane (aza-ylide) intermediate, which can react intramolecularly with an adjacent electrophilic group to produce a covalent amide bond.

Azido-reactive reagents of interest include, but are not limited to, dithiols and phosphines such as, arylphosphines (e.g., a triphenyl phosphine), alkylphosphines (e.g., a trialkylphosphine such as tris(2-carboxyethyl)phosphine (TCEP)), or arylalkylphosphines.

Reagents reactive with alkyne-modified amino acids

Any convenient reagents reactive with alkyne-modified D-amino acids may be utilized in the subject reagents and methods. Alkyne-reactive reagents of interest include, but are not limited to, click chemistry or copper-free click chemistry reagents, and azide-containing reagents.

In some instances, the azide-containing reagent is described by the formula:

wherein: L is a linker; and Y is a molecule of interest, e.g., a detectable label.

In some embodiments, L is (T)$_n$, where each n is a number selected from zero to 40; and where each T is a divalent moiety independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine.

Exemplary azide-containing groups that may be adapted for use in the subject reagents include, but are not limited to: azidoacetylmannosamine (ManNAz), azido-derivatized sugar (e.g., fucose), 5'-diphospho-6-azido-B-L-fucopyranoside, 3-azido-7-hydroxycoumarin, 4-azido-N-ethyl-1,8-naphthalimide, azide-linked biotin, azide-labelled antibody, an azide containing amino acid or peptide (e.g., azidogylcine or azidoalanine), etc.

A subject azide-containing reagent may be prepared using any convenient method, including but not limited to conversion of the amino group of an amine-containing reagent into an azide using any suitable method and chemistry. Methods to introduce an azide group are for example disclosed in WO03/003806.

Reagents reactive with norbornene-modified amino acids

Any convenient reagents reactive with norbornene-modified D-amino acids may utilized in the subject reagents and methods. Norbornene-reactive reagents of interest include, but are not limited to, hydrazonoyl chloride-containing reagents, photo-click reagents, tetrazole-containing reagents, tetrazine-containing reagents, reagents such as those described by Carell et al. "A Genetically Encoded Norbornene Amino Acid for the Mild and Selective Modification of Proteins in a Copper-Free Click Reaction", Angew. Chem. Int. Ed. 1012, 51, 4466-4469.

In some instances, the norbornene-reactive reagent is described by the formula:

wherein: L is a linker; W is a norbornene reactive functional group; and Y is a molecule of interest, e.g., a detectable label.

In some embodiments, L is (T)$_n$, where each n is a number selected from zero to 40; and where each T is a divalent moiety independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine.

In some instances, W is selected from a tetrazine, a tetrazole, a hydrazonyl chloride or a nitrile imine. In some cases, W is a functional group that is capable of reacting directly with a norbornene-modified D-amino acid. In other cases, W may first be activated by contact with a stimulus, such as a light stimulus or a chemical catalyst.

In some embodiments, the norbornene-reactive reagent is described by one of the following structures:

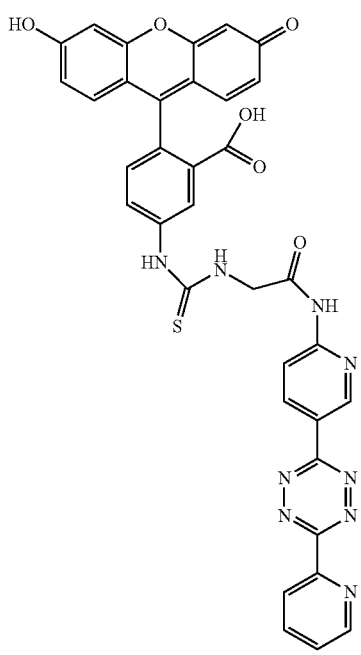

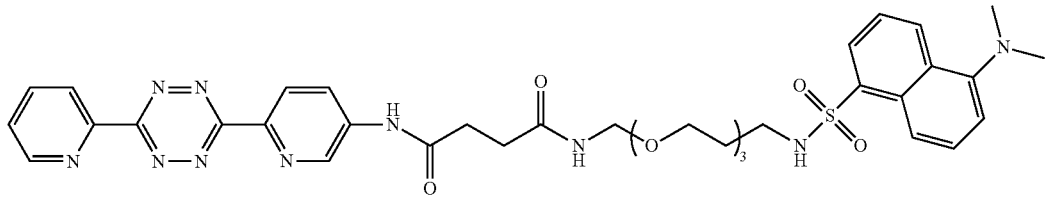

Modified peptidoglycan

In some embodiments, a modified PG is described by one of the following structures: PG-L-$N_3$ or PG-L-X where PG is a peptidoglycan, L is an optional linker, X is an alkyne group, a norbornene group or a tetrazole group (e.g., as described herein), and —$N_3$ is an azido group. In some instances, PG includes a D-amino acid residue. In certain instances, the azido or the alkyne or norbornene group X is connected to the D-amino acid residue of the PG via the optional linker L. As such, the D-amino acid residue may be referred to as a modified D-amino acid residue. The modified D-amino acid residue may be included at any convenient position of the PG sequence.

The modified PGs may be conjugated to a reagent, e.g., as described herein, convenient chemistry. Conjugation chemistries of interest include, but are not limited to, click chemistry, photo-click chemistry, tetrazine-click chemistry, and copper-free click chemistry, e.g., conjugations that include the [3+2] cycloaddition reaction of azide and alkyne functional groups to produce a 1,2,3-triazole linkage, or a reversed-electron-demand Diers-Alder reaction of a tetrazine and a norbornene functional group, or a photoinduced 1,3-dipolar cycloaddition reaction of a tetrazole and an alkene. In some instances, the modified PG includes an alkynyl group and the reagent includes an azido group. In other instances, the modified PG includes an azido group and the reagent includes an alkynyl group. In certain instances, the modified PG includes a norbornene group and the reagent includes a tetrazine or a tetrazole group. In certain cases, the modified PG includes a tetrazole group and the reagent includes an alkene. As such, in certain embodiments, a modified PG of the present disclosure may be labeled to include a PG linked to a molecule of interest via a heterocycle-containing linker, such as a triazole linker, a linker containing the product of a reversed-electron-demand Diers-Alder reaction, e.g., a norborene-tetrazine derived heterocycle containing linker as described herein, or a pyrazoline-containing linker.

In some instances, the labeled PG is described by the following formula:

PG-$L^1$-Z-$L^2$-Y where PG is a modified peptidoglycan; Y is a molecule of interest (e.g., a detectable label); $L^1$ and $L^2$ are independently optional linkers; and Z is a 1,2,3-triazole. The labeled PG may be derived from the conjugation of any convenient modified PG (e.g., as described herein) and any convenient alkynyl reagent or an azide-containing reagent (e.g., as described herein). In some cases, Y is a detectable label.

In certain cases, Z is a 1,2,3-triazole, a pyrazoline or the cycloaddition product of a norbornene and a tetrazine, a tetrazole or a hydrazonoyl chloride. In certain instances, Z is a norborene-tetrazine derived heterocycle described by the following structure:

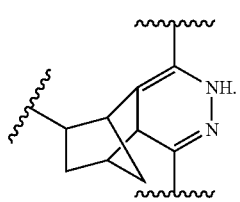 [SMILES: *C1=NNC(*)=C2C3CC(CC3*)C12]

In certain embodiments, the labeled PG includes a detectable label (e.g., a florescent label).

Detectable labels

Exemplary detectable labels include, but are not necessarily limited to, molecules (e.g., autofluorescent molecules, molecules that fluoresce upon contact with a reagent, etc.), radioactive labels (e.g., $^{111}$In, $^{125}$I, $^{131}$I, $^{212}$B, $^{90}$Y, $^{186}$Rh, and the like); biotin (e.g., to be detected through reaction of biotin and avidin); fluorescent tags; imaging reagents (e.g., those described in U.S. Pat. No. 4,741,900 and U.S. Pat. No. 5,326, 856), and the like. Detectable labels also include peptides or polypeptides that can be detected by antibody binding, e.g., by binding of a detectably labeled antibody or by detection of bound antibody through a sandwich-type assay. Also suitable for use are quantum dots (e.g., detectably labeled semiconductor nanocrystals, such as fluorescently labeled quantum dots, antibody-conjugated quantum dots, and the like). See, e.g., Dubertret et al. 2002 Science 298:759-1762; Chan et al. (1998) Science 281:2016-2018; U.S. Pat. No. 6,855,551; Bruchez et al. (1998) Science 281:2013-2016

Suitable fluorescent molecules (fluorophores) include, but are not limited to, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethylrhodamine-, methyl ester), TMRE (tetramethylrhodamine, ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl) phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino)naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino-1-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl)aminonaphthalene-1-sulfonic acid (EDANS),4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, and fluorescent europium and terbium complexes; and the like. Fluorophores of interest are further described in WO 01/42505 and WO 01/86001.

Suitable fluorescent proteins and chromogenic proteins include, but are not limited to, a green fluorescent protein (GFP), including, but not limited to, a GFP derived from Aequoria victoria or a derivative thereof, e.g., a "humanized" derivative such as Enhanced GFP, which is available commercially, e.g., from Clontech, Inc.; a GFP from another species such as Renilla reniformis, Renilla mulleri, or Ptilosarcus guernyi, as described in, e.g., WO 99/49019 and Peelle et al. (2001) J. Protein Chem. 20:507-519; "humanized" recombinant GFP (hrGFP) (Stratagene); any of a variety of fluorescent and colored proteins from Anthozoan species, as described in, e.g., Matz et al. (1999) Nature Biotechnol. 17:969-973; and the like.

Modified Bacteria

The present disclosure provides modified bacteria having incorporated into the PG of the bacteria modified PG (PG comprising a modified D-amino acid that includes a bioorthogonal functional group such as an azide, an alkyne, or a norbornene group), as described above.

Bacteria that can be modified such that PG present in the bacterial cell wall being synthesized comprises at least one modified D-amino acid include, but are not limited to, pathogenic intracellular bacteria (i.e., pathogenic bacteria that replicate in a host cell); pathogenic bacteria that do not replicate in a host cell; and non-pathogenic bacteria (e.g., non-pathogenic laboratory strains of bacteria). Non-pathogenic bacteria include commensal bacteria (present in a host) as well as free-living bacteria (living outside a host).

In some cases, the bacterium is an obligate intracellular pathogen or a facultative intracellular pathogen. Examples of such bacteria include, e.g., a Mycobacterium species. Examples of species of Mycobacterium include, but are not limited to, M. tuberculosis, M. bovis, M. bovis strain Bacillus calmette-guerin (BCG) including BCG substrains, M. avium, M. intracellulare, M. africanunum, M. kansasii, M. marinum, M. ulcerans and M. paratuberculosis. Examples of other obligate and facultative intracellular bacterial species include, but are not limited to, *Legionella pneumophila*, other *Legionella* species, *Salmonella typhi*, other *Salmonella* species, *Shigella* species, *Listeria monocytogenes*, *Staphylococcus aureus*, *Staphylococcus epidermidis*, *Bacteroides fragilis*, other *Bacteroides* species, *Chlamydia pneumoniae*, *Chlamydia trachomatis*, *Chlamydia psittaci*, *Coxiella burnetii*, other *Rickettsial* species, and *Ehrlichia* species.

Suitable bacteria include, but are not limited to, *Francisella tularensis*; *Listeria monocytogenes*; *Salmonella*; *Brucella*; *Legionella pneumophila*; *Mycobacterium* (e.g., *M. tuberculosis*, *M. leprae*, *M. bovis*, *M. avium*, *M. abscessus*); *Nocardia* (e.g., *N. asteroids*, *N. farcinica*, *N. nova*, *N. transvalensis*, *N. brasiliensis*, *N. pseudobrasiliensis*); *Rhodococcus equui*; *Yersinia pestis*; *Neisseria* (e.g., *N. meningitidis*, *N. gonorrhoeae*); *Shigella* (e.g., *S. dysenteriae*, *S. flexneri*, *S. boydii*, and *S. sonnei*); *Chlamydia* (*C. trachomatis*, *C. pneumoniae*, *C. psittaci*); *Rickettsia*; and *Coxsiella*. Other suitable bacteria include, e.g., pathogens such as *Vibrio cholerae*, *Pseudomonas aeruginosa*, and pathogenic *Escherichia coli*; model organisms such as *Escherichia coli*, *Bacillus subtilis*, and *Caulobacter cresentus*; facultative pathogens such as *Streptococcal* and *Clostridial* species; and commensals such as *Bacteroides thetaiotamicron*.

Methods oF Identifying Anti-Microbial Agents

The present disclosure provides methods of identifying anti-microbial agents, the methods generally involving: a) contacting a bacterial cell with a test agent; and b) determining the effect, if any, of the test agent on incorporation of a modified D-amino acid (a modified D-amino acid that includes a bioorthogonal functional group such as an azide, an alkyne, or a norbornene group, as described above) into peptidoglycan present in the bacterial cell. For the discussion below, a "modified D-amino acid" refers to a modified D-amino acid that includes a bioorthogonal functional group such as an azide, an alkyne, or a norbornene group, as described above.

Whether a test agent reduces incorporation of a-modified D-amino acid into PG present in a bacterial cell can be determined by contacting the bacterium with a reagent, as described above, which reacts with a modified D-amino acid present in the PG, where the reagent comprises a detectable label. In some cases, the detectable label is a fluorescent label. Where a test agent inhibits incorporation of a modified D-amino acid into PG present in a bacterial cell, the amount of label in the PG is reduced.

Test agents of interest include test agents that inhibit incorporation of a modified D-amino acid into the PG of a bacterial cell by at least about 10%, at least about 20%, at least about 25%, at least about 30%, at least about 40%, at least about 50%, at least about 60%, at least about 70%, at least about 80%, or more than 80%, compared to the extent of incorporation of the modified D-amino acid into the PG in the absence of the test agent. Test agents that inhibit incorporation of a modified D-amino acid into the PG of a bacterial cell are considered candidate anti-microbial agents.

In some embodiments, the bacterium is present in a eukaryotic cell-free liquid medium, i.e., the bacterium is not present intracellularly in a eukaryotic host cell. In other cases, the bacterium is present intracellularly in a eukaryotic host cell.

As noted above, in some instances, the bacterium is present intracellularly in a eukaryotic host cell. Suitable eukaryotic host cells include, but are not limited to, macrophages, monocytes, dendritic cells, and the like. Suitable cells include, e.g., eukaryotic cells, e.g., mammalian cells such as primary cells (e.g., bone marrow-derived macrophages; peripheral blood mononuclear cells; etc.). Suitable cells include, e.g., eukaryotic cells, e.g., mammalian cells such as human umbilical vein endothelial cells (HUVEC; e.g., American Type Culture Collection (ATCC)CRL-1730), human microvascular endothelial cells (HMEC-1; ATCC CRL-4025), PC3 cells (ATCC CRL1435), MDA-MB-231 cells (ATCC HTB26), MCF-7 cells (ATCC HTB22), HeLa cells (ATCC No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), and the like. In one non-limiting example, the cell used is a J774 macrophage cell line. In one non-limiting example, the cell used is the J774A.1 macrophage cell line (American Type Culture Collection (ATCC) TIB-67).

Suitable bacteria include, but are not limited to, facultative intracellular bacteria and obligate intracellular bacteria. Suitable bacteria include, but are not limited to, *Francisella tularensis*; *Listeria monocytogenes*; *Salmonella*; *Brucella*; *Legionella pneumophila*; *Mycobacterium* (e.g., *M. tuberculosis*, *M. leprae*, *M. bovis*, *M. avium*, *M. abscessus*); *Nocardia* (e.g., *N. asteroids*, *N. farcinica*, *N. nova*, *N. transvalensis*, *N. brasiliensis*, *N. pseudobrasiliensis*); *Rhodococcus equui*; *Yersinia pestis*; *Neisseria* (e.g., *N. meningitidis*, *N. gonorrhoeae*); *Shigella* (e.g., *S. dysenteriae*, *S. flexneri*, *S. boydii*, and *S. sonnei*); *Chlamydia* (*C. trachomatis*, *C. pneumoniae*, *C. psittaci*); *Rickettsia*; and *Coxsiella*. Other suitable bacteria include, e.g., pathogens such as *Vibrio cholerae*, *Pseudomonas aeruginosa*, and pathogenic *Escherichia coli*; model organisms such as *Escherichia coli*, *Bacillus subtilis*, and *Caulobacter cresentus*; facultative pathogens such as *Streptococcal* and *Clostridial* species; and commensals such as *Bacteroides thetaiotamicron*.

As used herein, the term "determining" refers to both quantitative and qualitative determinations and as such, the term "determining" is used interchangeably herein with "assaying," "measuring," and the like.

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 10,000 daltons, e.g., a candidate agent may have a molecular weight of from about 50 daltons to about 100 daltons, from about 100 daltons to about 150 daltons, from about 150 daltons to about 200 daltons, from about 200 daltons to about 500 daltons, from about 500 daltons to about 1000 daltons, from about 1,000 daltons to about 2500 daltons, from about 2500 daltons to about 5000 daltons, from about 5000 daltons to about 7500 daltons, or from about 7500 daltons to about 10,000 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample without the test agent (e.g., a sample the bacterial cell in the absence of the test agent). Generally a plurality of assay mixtures is run in parallel with different agent concentrations to obtain a differential response to the various concentrations. Typically, one of these concentrations serves as a negative control, i.e. at zero concentration or below the level of detection.

A variety of other reagents may be included in the screening assay. These include reagents such as salts, neutral proteins, e.g. albumin, detergents, etc., including agents that are used to facilitate optimal enzyme activity and/or reduce non-specific or background activity. Reagents that improve the efficiency of the assay, such as protease inhibitors, etc. may be used. The components of the assay mixture are added in any order that provides for the requisite activity. Incubations are performed at any suitable temperature, typically between 4° C. and 40° C. Incubation periods are selected for optimum activity, but may also be optimized to facilitate rapid high-throughput screening. Typically between 0.1 hour and 1 hour will be sufficient.

Immunomodulatory Compounds and Compositions

The present disclosure provides immunomodulatory compounds, and compositions comprising such compounds. A subject immunomodulatory compound comprises a PG fragment comprising a modified D-amino acid (a modified D-amino acid that includes a bioorthogonal functional group such as an azide, an alkyne, or a norbornene group, as described above) conjugated to a second compound (e.g., a conjugate partner). Suitable conjugate partners include, e.g., a therapeutic agent; an antigen; an allergen; a non-PG immunomodulatory agent; and the like. A subject immunomodulatory compound is useful for modulating (e.g., enhancing an immune response; reducing an immune response; shifting an immune response (e.g., shifting from a Th1 lymphocyte response to a Th2 lymphocyte response; shifting toward a Th17 lymphocyte response; etc.)) in an individual. In the discussion below, a "modified D-amino acid" refers to a modified D-amino acid that includes a bioorthogonal functional group such as an azide, an alkyne, or a norbornene group, as described above.

Suitable therapeutic agents include, but are not limited to, an anti-viral agent, an anti-bacterial agent, an anti-fungal agent, a cytokine, a hormone, an antibody, etc.

Suitable therapeutic agents include, but are not limited to, azathioprine, cyclosporin methothrexate, leflunomide, corticosteroids, cyclophosphamide, cyclosporine A, cyclosporin G, mycophenolate mofetil, ascomycin, rapamycin (sirolimus), FK-506, mizoribine, deoxyspergualin, brequinar, mycophenolic acid, malononitriloamindes (e.g., leflunamide), T cell receptor modulators, and cytokine receptor modulators, peptide mimetics, and antibodies (e.g., human, humanized, chimeric, monoclonal, polyclonal, Fvs, ccFvs, Fab, single domain antibodies (nanobodies), or F(ab)$_2$ fragments or epitope binding fragments), nucleic acid molecules (e.g., antisense nucleic acid molecules, siRNA, and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boehringer), IDEC-CE9.1™ (IDEC and SKB), mAB 4162W94, Orthoclone and OKTcdr4a (Janssen-Cilag)), anti-CD3 antibodies (such as, by way of example only, Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), anti-B7 antibodies (e.g., IDEC-114 (IDEC)), CTLA4-immunoglobulin, and other toll receptor-like (TLR) modulators. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), and anti-IL-12 antibodies).

Suitable cytokines and modulators of cytokine function include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, alpha-, beta-, and gamma-interferon, interferon β-1a, interferon β-1b, interferon α-1, interferon α-2a (roferon), interferon α-2b, pegylated interferons (by way of example only, peginterferon α-2a and peginterferon α-2b), intron, Peg-Intron, Pegasys, consensus interferon (infergen), albumin-interferon α and albuferon.

Suitable antigens include, antigens derived from infectious agents (e.g., bacterial, fungal (including unicellular and multicellular), and viral infectious agents); tumor antigens; and the like. Examples of pathogens include, but are not limited to, viruses, e.g., herpes simplex virus (HSV), hepatitis A virus, hepatitis B virus (HBV), hepatitis C virus (HCV), cytomegalovirus (CMV), dengue virus, flavivirus, Epstein-Barr virus (EBV), influenza virus, measles virus, human immunodeficiency virus (HIV), human papilloma virus (HPV), Japanese encephalitis virus, norovirus, polio virus, rotavirus, respiratory syncytial virus (RSV), ebola virus, rabies virus, Sendai virus, severe acute respiratory syndrome (SARS) coronavirus, smallpox virus, West Nile virus, yellow fever virus; bacteria, e.g., *Mycobacterium tuberculosis* (tuberculosis), *Chlamydia trachomatis* (trachoma), *Haemophilus influenzae* (otitis media), *Neisseria meningitidis* (meningitis), *Streptococcus pneumoniae* (pneumonia), *Escherichia coli* (intestinal disorders) *Staphylococcus aureus, Bacillus anthracis* (anthrax), *Borrelia burgdorferi* (Lyme's disease); and parasites, e.g., *Plasmodium* (malaria), *Leishmania, Trypanosoma cruzi, Trypanosoma brucei, Ascaris lumbricoides*

(ascariasis), hookworm, *Onchocerca volvulus* (river blindness), *Schistosoma* (schistosomasis), *Trichuris trichiura* (trichurasis).

Suitable allergens include, but are not limited to, allergens such as reactive major dust mite allergens Der pI and Der pII; T cell epitope peptides of the Der pII allergen; Amb al ragweed pollen allergen; phospholipase A2 (bee venom) allergen and T cell epitopes; white birch pollen (Betyl); the Fel dI major domestic cat allergen; tree pollen; grass pollen; inhaled allergens (e.g., grass, weed, and tree pollens, mold spores, chemicals, cockroach calyx, dust mite excretions, animal dander, saliva); ingested allergens (e.g., food, food supplements, home remedies, medications); contact allergens (e.g., cosmetics, fragrances, plants, detergents, chemicals, metals, latex); and injected allergens (e.g., medications, insect venom).

A subject immunomodulatory compound can be administered orally as discrete dosage forms, wherein such dosage forms include, but are not limited to, capsules, gelatin capsules, caplets, tablets, chewable tablets, powders, granules, syrups, flavored syrups, solutions or suspensions in aqueous or non-aqueous liquids, edible foams or whips, and oil-in-water liquid emulsions or water-in-oil liquid emulsions.

The capsules, gelatin capsules, caplets, tablets, chewable tablets, powders or granules, used for the oral administration of a subject immunomodulatory compound are prepared by admixing a subject immunomodulatory compound (active ingredient) together with at least one excipient using conventional pharmaceutical compounding techniques. Non-limiting examples of excipients used in oral dosage forms described herein include, but are not limited to, binders, fillers, disintegrants, lubricants, absorbents, colorants, flavors, preservatives and sweeteners.

Non-limiting examples of suitable binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof.

Non-limiting examples of suitable fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein are present in from about 50 to about 99 weight percent of the pharmaceutical composition or dosage form.

Non-limiting examples of suitable disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain embodiments, the amount of disintegrant used in the pharmaceutical compositions provided herein is from about 0.5 to about 15 weight percent of disintegrant, while in other embodiments the amount is from about 1 to about 5 weight percent of disintegrant.

Non-limiting examples of suitable lubricants include, but are not limited to, stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and combinations thereof. In certain embodiments, the amount of lubricants used in the pharmaceutical compositions provided herein is in an amount of less than about 1 weight percent of the pharmaceutical compositions or dosage forms.

Non-limiting examples of suitable diluents include, but are not limited to, lactose, dextrose, sucrose, mannitol, sorbitol, cellulose, glycine or combinations thereof.

In certain embodiments, a subject immunomodulatory compound is orally administered as a controlled release dosage form. Such dosage forms are used to provide slow or controlled-release of a subject immunomodulatory compound. Controlled release is obtained using, for example, hydroxypropylmethyl cellulose, other polymer matrices, gels, permeable membranes, osmotic systems, multilayer coatings, microparticles, liposomes, microspheres, or a combination thereof.

Administration of a subject immunomodulatory compound as oral fluids such as solution, syrups and elixirs are prepared in unit dosage forms such that a given quantity of solution, syrups or elixirs contains a predetermined amount of a subject immunomodulatory compound. Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

In certain embodiments, pharmaceutical compositions comprising a subject immunomodulatory compound are administered parenterally by various routes including, but not limited to, subcutaneous, intravenous (including bolus injection), intramuscular, and intraarterial.

Parenteral dosage forms are administered in the form of sterile or sterilizable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In certain embodiments, pharmaceutical compositions comprising a subject immunomodulatory compound are administered transdermally. Such transdermal dosage forms include "reservoir type" or "matrix type" patches, which are applied to the skin and worn for a specific period of time to permit the penetration of a desired amount of a subject immunomodulatory compound. By way of example only, such transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In other embodiments, matrix transdermal formulations are used.

Formulations for transdermal delivery of a subject immunomodulatory compound include an effective amount of a subject immunomodulatory compound, a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof.

In certain embodiments, such transdermal delivery systems include penetration enhancers to assist in delivering a subject immunomodulatory compound to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other embodiments, the pH of such a transdermal pharmaceutical composition or dosage form, or of the tissue to which the pharmaceutical composition or dosage form is applied, is adjusted to improve delivery of a subject immunomodulatory compound. In other embodiments, the polarity of a solvent carrier, its ionic strength, or tonicity is adjusted to improve delivery. In other embodiments, compounds such as stearates are added to advantageously alter the hydrophilicity or lipophilicity of a subject immunomodulatory compound so as to improve delivery. In certain embodiments, such stearates serve as a lipid vehicle for the formulation, as an emulsifying agent or surfactant, and as a delivery-enhancing or penetration-enhancing agent. In other embodiments, different salts, hydrates or solvates of a subject immunomodulatory compound are used to further adjust the properties of the resulting composition.

In certain embodiments, pharmaceutical compositions comprising a subject immunomodulatory compound are administered nasally. The dosage forms for nasal administration are formulated as aerosols, solutions, drops, gels or dry powders. In certain embodiments pharmaceutical compositions comprising a subject immunomodulatory compound are administered rectally in the form of suppositories, enemas, ointment, creams rectal foams or rectal gels. In certain embodiments such suppositories are prepared from fatty emulsions or suspensions, cocoa butter or other glycerides.

Methods of Modulating an Immune Response

The present disclosure provides methods of modulating an immune response in an individual, the methods generally involving administering to an individual in need thereof an effective amount of an immunomodulatory compound or composition, as described above.

An "effective amount" of a subject immunomodulatory compound or composition is an amount that, when administered to an individual in one or more doses, is effective to modulate an immune response in the individual. For example, in some case, an "effective amount" of a subject immunomodulatory compound or composition is an amount that, when administered to an individual in one or more doses, is effective to increase the number of T lymphocytes (e.g., T helper cells, cytotoxic T cells, or any T cell subset) in the individual by at least about 10%, at least about 25%, at least about 50%, at least about 75%, at least about 2-fold, at least about 5-fold, at least about 10-fold, or more than 10-fold, compared to the number of T lymphocytes in the individual before administration of the subject immunomodulatory compound or composition.

As another example, in some cases, an "effective amount" of a subject immunomodulatory compound or composition is an amount that, when administered to an individual in one or more doses, is effective to increase the number of B cells in the individual by at least about 10%, at least about 25%, at least about 50%, at least about 75%, at least about 2-fold, at least about 5-fold, at least about 10-fold, or more than 10-fold, compared to the number of B cells in the individual before administration of the subject immunomodulatory compound or composition.

As another example, in some cases, an "effective amount" of a subject immunomodulatory compound or composition is an amount that, when administered to an individual in one or more doses, is effective to increase the amount of circulating immunoglobulin in the individual by at least about 10%, at least about 25%, at least about 50%, at least about 75%, at least about 2-fold, at least about 5-fold, at least about 10-fold, or more than 10-fold, compared to the level of circulating immunoglobulin in the individual before administration of the subject immunomodulatory compound or composition.

Suitable routes of administration include, e.g., parenteral and enteral routes of administration. Suitable routes of administration include, but are not limited to, intranasal, oral, mucosal, sublingual, transdermal, and transmucosal. A subject immunomodulatory compound or composition can be administered via oral administration, rectal administration, parenteral, intravenous administration, intravitreal administration, intramuscular administration, inhalation, intranasal administration, topical administration, ophthalmic administration, or otic administration.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Preparation of Cyclooctyne-Functionalized D-Amino Acids

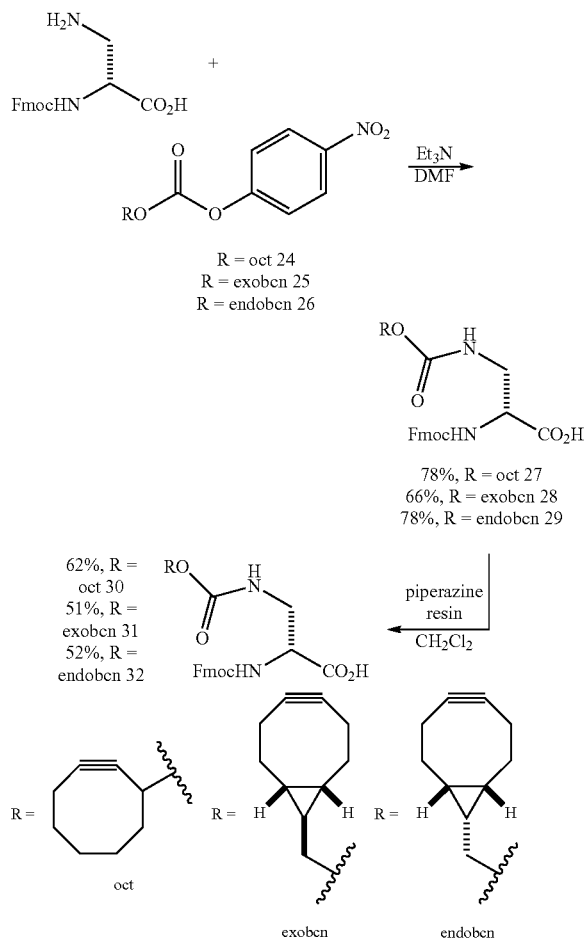

Cyclooctyne-functionalized D-amino acids are prepared from Fmoc-protected D-diaminopropionic acid, which are prepared in one step from commercially available Fmoc-D-asparagine using a procedure as described by Lau et al. (Synlett 2011, 13, 1917-1919) (Scheme 1). The Fmoc-protected D-diaminopropionic acid was then coupled to cyclooctynol-para-nitrophenol carbonates 24 to 26 to generate Fmoc-protected cyclooctyne D-amino acids 27 to 29 using methods as described by Plass et al. (Angew. Chem. Int. Ed. 2011, 50, 3878-3881) and Dommerholt et al. (Angew. Chem. Int. Ed. 2010, 49, 9422-9425). Finally, these compounds were deprotected using piperazine resin in $CH_2Cl_2$ to yield the cyclooctyne amino acids 30 (octDala), 31 (exobcnDala), and 32 (endobcnDala).

With all three amino acids in hand, their incorporation into the peptidoglycan of gram-positive bacteria was tested. The bacteria were grown for one-doubling time in the presence of 5 mM unnatural amino acids 30 to 32. The cells were then washed to remove excess amino acid and labeled with 20 μM of the commercially available azido-PEG3-carboxyrhodamine. This fluorophore efficiently labels terminal-alkyne-tagged peptidoglycan under copper-click conditions. The cells were then washed to remove excess probe, fixed, and studied by flow-cytometry and microscopy. Labeling was observed for all three unnatural cyclooctyne analogues, with the relative labeling tracking with the kinetics of the parent cyclooctynes. The labeling was shown to be comparable to that used for TBTA plus the linear alkyne D-propargylglycine (alkDala), with the advantage that this labeling can occur in the absence of copper. Microscopy showed that labeling was limited to the cell wall, consistent with incorporation of the amino acid into peptidoglycan.

To further confirm that peptidoglycan was being labeled, a competition experiment was performed. Incubation of *L. monocytogenes* with cyclooctyne D-amino acid in the presence of excess D-alanine resulted in a decrease in fluorescence after labeling. Additionally, *listeria* lacking PBP5 also showed enhanced labeling over wild type. This enhancement is comparable for both the relatively small alkDala and the bulkier cyclooctyne amino acids, suggesting that the PBP5 enzyme is tolerant of larger, unnatural substrates.

Example 2

Incorporation of Azide- and Alkyne-Modified D-Amino Acids into Peptidoglycan This disclosure describes a chemical approach for probing PG in vivo via metabolic labeling and bioorthogonal chemistry. A wide variety of bacterial species incorporated azide and alkyne-functionalized D-alanine into their cell walls, which we visualized by covalent reaction with click chemistry probes. The D-alanine analogs were specifically incorporated into nascent PG of the intracellular pathogen *Listeria monocytogenes* both in vitro and during macrophage infection. Metabolic incorporation of D-alanine derivatives and click chemistry detection constitute a facile, modular platform that facilitates unprecedented spatial and temporal resolution of PG dynamics in vivo.

Materials And Methods

In vitro D-Alanine Derivative Labeling. The origin and identity of bacterial strains are detailed in Supporting Information. Alexa Fluor 350 succiminidyl-ester (Invitrogen) was prepared exactly as described.(35) Vancomycin-BODIPY (Invitrogen) was used as a 1:1 mixture with unlabeled vancomycin at a final concentration of 1 μg/ml. D-alanine derivatives were used at 0.5-10 mM for labeling in vitro and 5-50 mM for labeling in macrophages. Analysis of PG by HPLC and mass spectrometry is included in Supporting Information. Strain-promoted cycloaddition was performed using 1 μM or 10 μM of BARAC(36) or DIFO(37) conjugates, respectively. CuAAC was performed on cell surfaces and lysates as described(38) using 20 μM of azide or alkyne conjugate. For cell surface labeling, we obtained the best results when bacteria were fixed with 2% formaldehyde prior to the click reactions. The Staudinger ligation was performed by incubating cell lysates in 500 μM phosphine-FLAG(39) overnight at 37° C.

Figure 3:
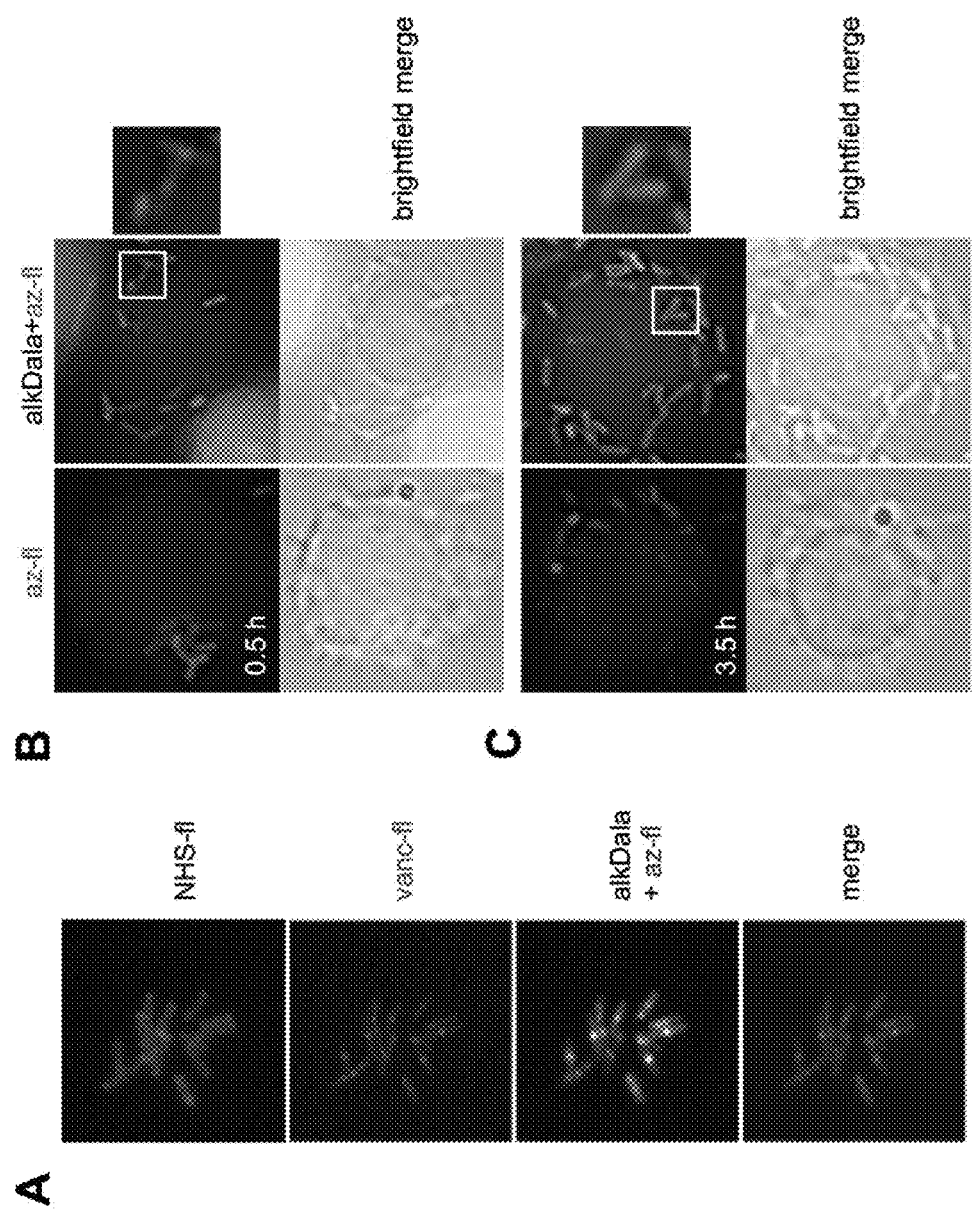
FIGS. 3A-C depict labeling of newly synthesized *L. monocytogenes* PG by alkDala in vitro and in vivo.

Imaging analysis. Details on microscopy are provided in Supporting Information. For multi-color images (FIG. 3), fluorescence intensities were adjusted in SLIDEBOOK software (Intelligent Imaging Innovations) to images of both untreated, non-fluorescent control cells as well as controls labeled with a single reagent or fluorophore. Contrast was increased equally across the greyscale images in Image™ Images stacks for FIG. 3B were made into a z-projection image using the average setting and deconvolved in ImageJ using PSF generator and iterative deconvolver plugins developed by OptiNav, Inc. Separate channel images were merged together to form an RCSB composite. For single-color images (FIG. 1C), fluorescence intensities were normalized to controls lacking alkDala or azDala in SLIDEBOOK software.

In vivo D-Alanine derivative labeling. *L. monocytogenes* were grown overnight at 30° C. without shaking. The next day, the bacteria were washed in PBS then added to J774 cells growing in chamber slides at a multiplicity of infection of 10. After 30 min, the coculture was washed in PBS and incubated in fresh medium. Gentamicin was added after an additional 30 min and alkDala was added either 30 min or 3.5 h after addition of bacteria. After 4 h cells were washed in PBS then incubated 3×5 min in fresh, pre-warmed medium containing gentamicin but not D-alanine derivative. The coculture was washed in PBS, fixed in 4% formaldehyde and permeabilized with 1% Triton-X. The CuAAC reaction was performed with azido-fluor 488 for 30 min. The slides were mounted in Vectashield (Vector Labs) for imaging.

Results

Efforts were made to determine whether D-amino acids bearing bioorthogonal functional groups could be used for metabolic labeling. Azides and alkynes are small chemical reporters that are stable in and absent from biological systems.(19) They undergo selective reaction with each other and, in the case of the azide, with phosphines and strained cyclooctynes as well.(19) To evaluate the ability of unnatural D-alanine derivatives to access the cell wall, bacteria were grown in media containing R-propargylglycine (compound 1, FIG. 1B, abbreviated alkDala) or R-2-amino-3-azidopropanoic acid (compound 2, FIG. 1B, abbreviated azDala). The cells were then reacted with a complementary fluorescent dye using strain-promoted cycloaddition or copper-catalyzed azide-alkyne cycloaddition (CuAAC)(19) (FIG. 1B). Clear cell surface labeling of all species tested (FIG. 1C), including several Gram-positive bacteria, one Gram-negative and *Mycobacterium tuberculosis*, a Gram-positive with an unusually complex cell wall, was observed by microscopy. The concentrations of D-alanine analog used for labeling did not inhibit bacterial growth.

The studies focused on the facultative intracellular pathogen *L. monocytogenes* for further characterization of D-alanine analog metabolism AlkDala labeling of wildtype *L. monocytogenes* was compared to that of a D-alanine auxotroph (termed dal⁻ dat⁻).(20) The auxotroph, which is unable to synthesize natural D-alanine as an endogenous competitor of the synthetic substrate, labeled more strongly (FIG. 1D). Similarly, addition of exogenous D-alanine suppressed azDala labeling (FIG. 1E). These results suggest that alkDala and azDala access the same metabolic pathways as natural D-alanine.

FIGS. 1A-E. Incubation of bacteria in D-alanine analogs followed by reaction with click chemistry probes results in cell surface fluorescence. (A) Chemical structure of *Escherchia coli* and *Listeria monocytogenes* PG (mDAP=meso-diaminopimelic acid). Newly synthesized disaccharide pentapeptides are substrates for penicillin-binding protein (PBP) processing, including cross-linking by transpeptidases (TPases) and trimming by carboxypeptidases (CPases). (B) Schematic representation of in vitro metabolic labeling with D-alanine analogs (1, 2) followed by click chemistry detection (3-6). R-propargylglycine (1, alkDala), 2-amino-3-azidopropanoic acid (2, azDala), azide (3) and alkyne (4) conjugates for Cu(I)-catalyzed azide-alkyne cycloaddition (CuAAC), cyclooctyne probe for strain-promoted cycloaddition (5), phosphine reagent for Staudinger ligation (6). The identity of the green star varies according to application e.g. fluorophores or affinity handles. (C) Clockwise from top left: *E. coli* (Ec), *Bacillus subtilis* (Bs), *L. monocytogenes* (Lm), *Mycobacterium tuberculosis* (Mt), *Streptomyces coelicolor* (Sc), *Corynebacterium glutamicum* (Cg). Scale bars, 1 μm. (D) The dal⁻ dat⁻ D-alanine auxotroph labels better than wildtype *L. monocytogenes* with alkDala, CuAAC. MFI, mean fluorescence intensity. (E) 2 mM D- but not L-alanine competes labeling by 5 mM azDala, strain-promoted cycloaddition in dal- dat- *L. monocytogenes*. The mutant was supplemented with an additional 1 mM D-alanine in all conditions for (E). Error bars for (D) and (E), +/−s.d. *P=0.0002 for (D), *P=2×10⁻⁵ for (E), two-tailed Student's t tests. Data are in triplicate and representative of four and two experiments, respectively.

It was hypothesized that there are three potential sites of D-alanine analog incorporation: proteins, lipoteichoic acids (LTA) and PG. The first would likely require both racemization and a highly promiscuous aminoacyl tRNA synthetase. (21, 22) To address this possibility directly, lysates from azDala-treated *L. monocytogenes* were reacted with alkyne-biotin and analyzed the products by immunoblot. No azide-labeled proteins were detected. Although D-alanine incorporation systems for LTA are generally very specific,(23) the second theoretical possibility that D-alanine analogs might label this biopolymer was addressed. LTA enriched from azDala-treated *L. monocytogenes* was reacted with phosphine-FLAG and probed by immunoblot as above. No azide-labeled species was detected in these cell wall preparations. Furthermore, a mutant that does not produce LTA(24) labeled with identical efficiency to wildtype bacteria. These data suggest that the D-alanine derivatives do not incorporate into proteins or LTA. D-alanylation of the other *L. monocytogenes* teichoic acid polymer, wall teichoic acid (WTA), has not been observed.(25, 26)

Figure 2:
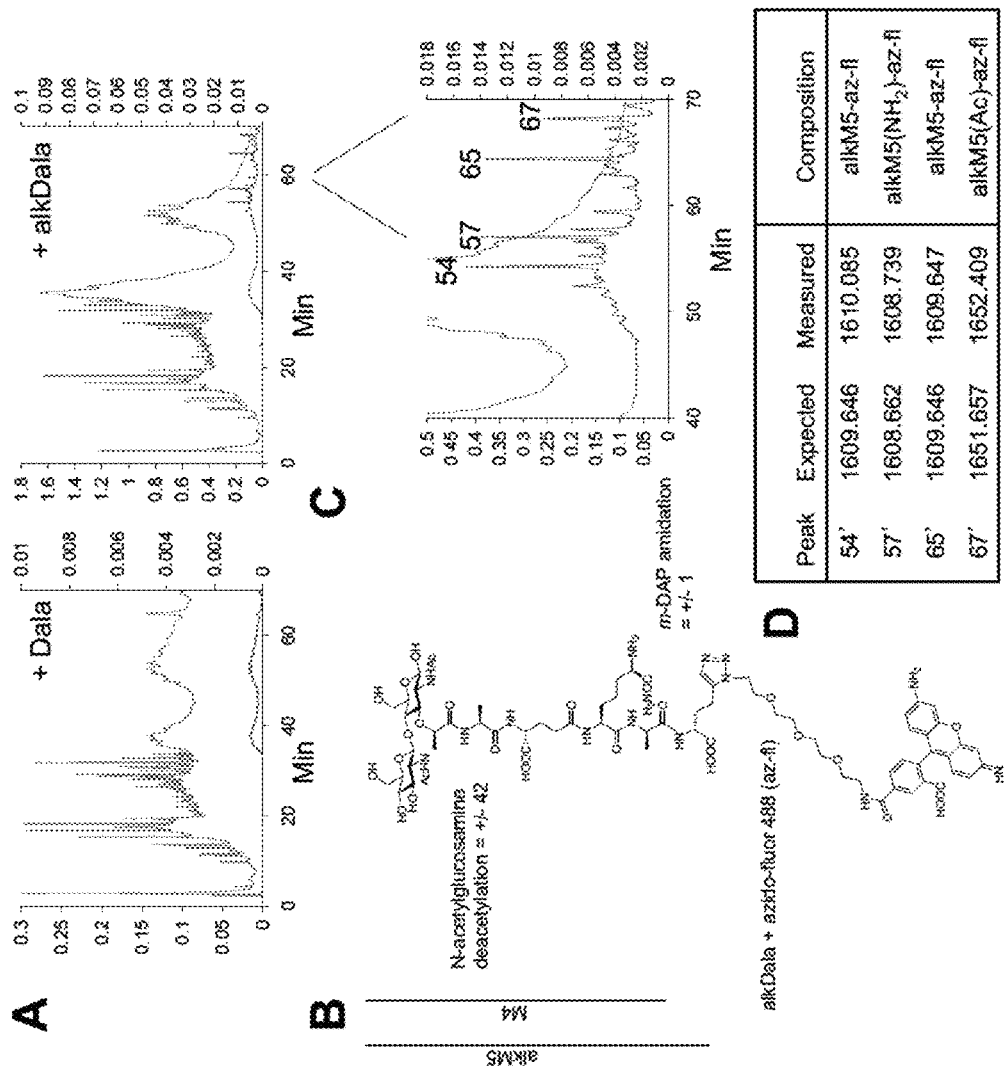
FIGS. 2A-D depict incorporation of alkyne-modified D-alanine (alkDala) into *L. monocytogenes* PG.

Having ruled out other potential sites of D-alanine derivative labeling, direct evidence of its incorporation into PG was sought. PG comprises a repeating disaccharide to which is conjugated a short peptide, termed the stem peptide (FIG. 1A). Although newly synthesized PG stem peptide usually terminates in D-alanine-D-alanine, diverse bacterial phyla produce and incorporate D-amino acids other than D-alanine into those positions. (17, 18) The process is flexible; various natural and unnatural D-amino acids appear to incorporate, albeit at varying efficiencies.(16-18) To test whether D-alanine derivatives incorporate into PG, *Escherchia coli* or *L. monocytogenes* was incubated with alkDala; afterwards, the cells were reacted with azido-fluor 488, and PG was purified from the cells for further analysis. After digesting the PG with muramidase, HPLC was used to detect muropeptides by absorbance at either 204 nm (to visualize all species) or 500 nm (to identify fluorophore-containing fragments). Finally the most abundant peaks at 500 nm were collected, and mass spectrometry was used to assign their chemical structures. This analysis showed that alkDala inserts into the fourth position of the stem peptide in *E. coli* PG and the fifth position in *L. monocytogenes* PG (FIG. 2). PG samples from *E. coli* incubated in azDala alone were analyzed; and it was determined that the fraction of D-alanine that had been replaced with the synthetic analog was roughly 50% of the tetrapeptide pool and 15% of the total muropeptide population. Importantly, even long periods of alkDala incubation did not appreciably change PG structure compared to D-alanine incubation performed in parallel.

FIGS. 2A-D. AlkDala incorporates into *L. monocytogenes* PG. (A) HPLC chromatograms of non-reduced muropeptides from *L. monocytogenes* incubated in the presence of 5 mM D-alanine (left) or alkDala (right) then reacted with azido-fluor 488. Absorbance at 204 nm, blue, and at 500 nm, red, are shown. The trace for the alkDala-treated sample is enlarged in (C). The most abundant peaks detected at 500 nm were collected and subjected to analysis by mass spectrometry, (D), to identify the chemical structure of the alkDala-containing muropeptides conjugated to azido-fluor 488, (B).

The positional selectivity of alkDala in PG implies a biosynthetic pathway of incorporation. There are two primary mechanisms for insertion of D-amino acids into PG: periplasmic editing of the mature polymer and cytosolic incorporation into PG precursors.(18, 27) The first process is an L,D- or D,D-transpeptidation reaction that, respectively, results in a new D-amino acid at the fourth or fifth position of the PG stem peptide. The second process is catalyzed by intracellular ligases and results in a new D-amino acid only at the fifth position. The pentapeptide substrates that support D,D-transpeptidase incorporation of D-amino acids in other bacteria are short-lived in *L. monocytogenes* because they are rapidly lost during PG maturation (FIG. 1A,(28-30)). Thus the observation of alkDala in the fifth position suggests that D-alanine analogs incorporate into newly synthesized *L. monocytogenes* PG. Three additional lines of evidence support this notion. First, D-alanine analog labeling was greatest at the peak of new cell wall production, in exponential phase growth. Next, incubating *L. monocytogenes* in alkDala for one generation followed by reaction with azido-fluor 545 resulted in signal that colocalized with that of vancomycin-BODIPY, a marker of nascent PG (FIG. 3A,(8)). Finally, treatment of bacteria with fosfomycin, a drug that inhibits PG synthesis very early in the pathway, completely abrogated alkDala labeling, whereas treatment with penicillin and meropenem, antibiotics that target periplasmic editing enzymes, had a much weaker effect.

*L. monocytogenes* naturally infects macrophages where it can escape from the phagosome and proliferate in the cytosol. The dal⁻ dat⁻ D-alanine auxotroph shows wildtype infectivity in cultured cells when D-alanine is added to the tissue culture medium.(20) This observation suggests that D-alanine and perhaps other D-amino acids are effectively taken up by macrophages at levels sufficient to support *L. monocytogenes* growth. Moreover, because eukaryotic cells do not generally produce D-amino acids, it was reasoned that D-alanine analogs might selectively label bacteria inside of host cells. To test this hypothesis, J774 macrophages were infected with *L. monocytogenes*, removed extracellular bacteria and treated the coculture with alkDala. Cells were incubated in alkDala for less than one *L. monocytogenes* generation, to label newer PG, or for several generations, to label both new and mature PG. Chemical methods, used previously for labeling intracellular proteins in mammalian cells (31, 32), were adapted to visualize PG by reaction with azido-fluor 488. Alkyne-dependent signal varied according to alkDala incubation time: *L. monocytogenes* labeled more at the septa when incubated for a short pulse and at the septa and poles when labeled for a longer one (FIG. 3B). The spatial distribution of fluorescence approximated that observed on bacteria grown alone in vitro (FIG. 1C, top right).

FIGS. 3A-C. AlkDala labels newly synthesized *L. monocytogenes* PG in vitro and in vivo. (A) Fluorescent signals from vancomycin-BODIPY (vanc-fl) and alkDala, azido-fluor 545 (az-fl) colocalize. *L. monocytogenes* were incubated in Alexa Fluor 350 succiminidyl-ester (NHS-fl) to non-specifically label cell wall proteins then washed and resuspended in alkDala for 1 hr and vanc-fl for the last 30 min. (B), (C) AlkDala labels intracellular *L. monocytogenes*. J774 cells were infected with *L. monocytogenes* bearing red fluorescent protein (RFP) under the actA promoter (34). Because this promoter is regulated by PrfA and induced upon escape from the phagosome, RFP expression correlates with entry into the cytosol (34). Extracellular bacteria were washed away after 30 min and the infected cells were incubated in fresh medium containing gentamicin. 50 mM alkDala was added for the remaining 3.5 hrs (C) or for the last 30 minutes only (B). Infected cells were fixed, permeabilized and reacted with azido-fluor 488. Top rows, fluorescent images, bottom rows, fluorescent and brightfield merge.

Although the method was developed using *L. monocytogenes*, the D-alanine analogs incorporate into a wide variety of bacteria and will promote investigation of diverse PG dynamics both in vitro and during infection. Furthermore, D-alanine analogs will greatly expand the scope of PG analysis. Judicious use of the ever-expanding azide and alkyne-reactive probe kit should permit integration of biochemical, genetic and cell biological data that historically have been collected and analyzed in isolation. Multi-tiered interrogation of PG in the host environment may uncover new avenues for inhibiting this well-validated drug target.

Figure 4:
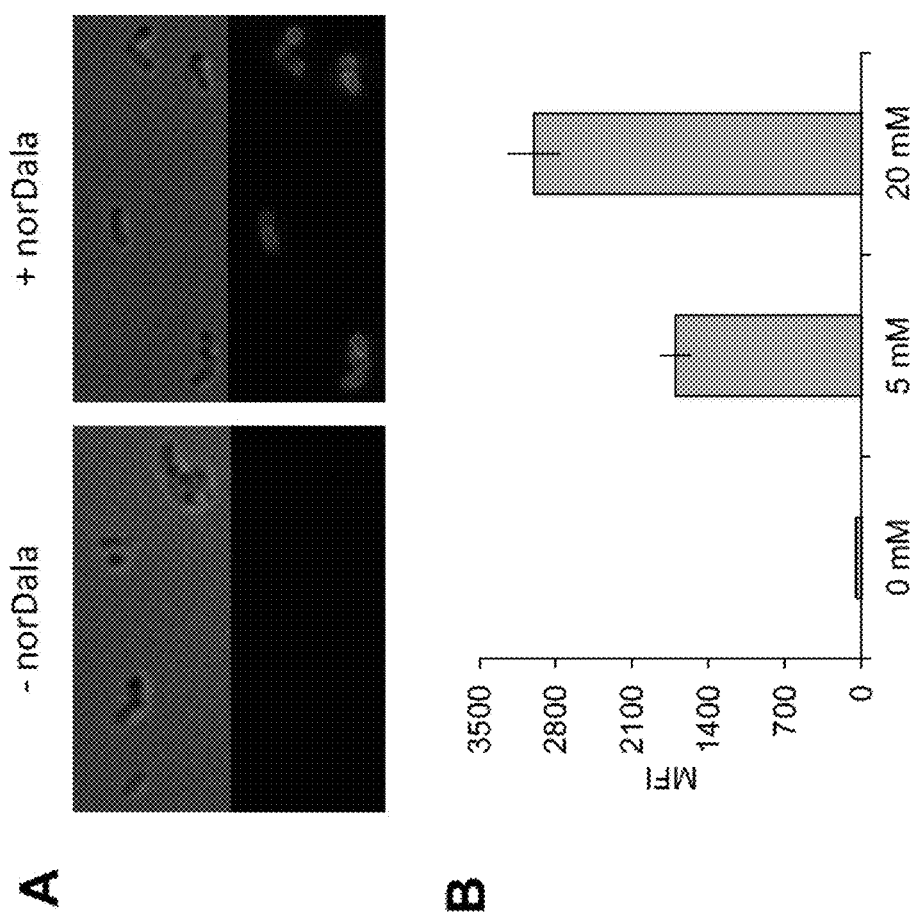
FIG. 4A-B depicts cell surface fluorescence resulting from incubation of bacteria in norbornene-D-alanine (norDala) followed by conjugation with tetrazine-fluorescein.

FIG. 4 depicts labeling of *C. glutamicum* grown in the presence or absence of 20 mM norbornene-D-alanine (norDala) for three doublings, washed then incubated in 10 uM tetrazine-fluorescein for 1 hr prior to imaging. FIG. 4B, *C. glutamicum* grown in the presence or absence of 5 mM or 20 mM norDala, detected as above then subjected to flow cytometry to quantitate fluorescence intensity. MFI, mean fluorescence intensity. Error bars, +/−s.d.

REFERENCES

1. Typas, A., Banzhaf, M., Gross, C. A., and Vollmer, W. (2012) From the regulation of peptidoglycan synthesis to bacterial growth and morphology, *Nat Rev Microbiol* 10, 123-136.
2. Quintela, J. C., de Pedro, M. A., Zollner, P., Allmaier, G., and Garcia-del Portillo, F. (1997) Peptidoglycan structure of *Salmonella typhimurium* growing within cultured mammalian cells, *Mol Microbiol* 23, 693-704.
3. Davis, K. M., and Weiser, J. N. (2011) Modifications to the peptidoglycan backbone help bacteria to establish infection, *Infect Immun* 79, 562-570.
4. Scheffers, D. J., and Pinho, M. G. (2005) Bacterial cell wall synthesis: new insights from localization studies, *Microbiol Mol Biol Rev* 69, 585-607.
5. Park, J. T., and Uehara, T. (2008) How bacteria consume their own exoskeletons (turnover and recycling of cell wall peptidoglycan), *Microbiol Mol Biol Rev* 72, 211-227, table of contents.
6. Glauner, B. (1988) Separation and quantification of muropeptides with high-performance liquid chromatography, *Anal Biochem* 172, 451-464.
7. Sizemore, R. K., Caldwell, J. J., and Kendrick, A. S. (1990) Alternate gram staining technique using a fluorescent lectin, *Appl Environ Microbiol* 56, 2245-2247.
8. Daniel, R. A., and Errington, J. (2003) Control of cell morphogenesis in bacteria: two distinct ways to make a rod-shaped cell, *Cell* 113, 767-776.
9. Tiyanont, K., Doan, T., Lazarus, M. B., Fang, X., Rudner, D. Z., and Walker, S. (2006) Imaging peptidoglycan biosynthesis in *Bacillus subtilis* with fluorescent antibiotics, *Proc Natl Acad Sci USA* 103, 11033-11038.

10. de Pedro, M. A., Quintela, J. C., Holtje, J. V., and Schwarz, H. (1997) Murein segregation in *Escherichia coli, J Bacteriol* 179, 2823-2834.
11. Viala, J., Chaput, C., Boneca, I. G., Cardona, A., Girardin, S. E., Moran, A. P., Athman, R., Memet, S., Huerre, M. R., Coyle, A. J., DiStefano, P. S., Sansonetti, P. J., Labigne, A., Bertin, J., Philpott, D. J., and Ferrero, R. L. (2004) Nod1 responds to peptidoglycan delivered by the *Helicobacter pylori* cag pathogenicity island, *Nat Immunol* 5, 1166-1174.
12. Sadamoto, R., Niikura, K., Sears, P. S., Liu, H., Wong, C. H., Suksomcheep, A., Tomita, F., Monde, K., and Nishimura, S. (2002) Cell-wall engineering of living bacteria, *J Am Chem Soc* 124, 9018-9019.
13. Nelson, J. W., Chamessian, A. G., McEnaney, P. J., Murelli, R. P., Kazmierczak, B. I., and Spiegel, D. A. (2010) A biosynthetic strategy for re-engineering the *Staphylococcus aureus* cell wall with non-native small molecules, *ACS Chem Biol* 5, 1147-1155.
14. Olrichs, N. K., Aarsman, M. E., Verheul, J., Arnusch, C. J., Martin, N. I., Herve, M., Vollmer, W., de Kruijff, B., Breukink, E., and den Blaauwen, T. (2011) A novel in vivo cell-wall labeling approach sheds new light on peptidoglycan synthesis in *Escherichia coli, Chembiochem* 12, 1124-1133.
15. Cabeen, M. T., and Jacobs-Wagner, C. (2005) Bacterial cell shape, *Nat Rev Microbiol* 3, 601-610.
16. Caparros, M., Pisabarro, A. G., and de Pedro, M. A. (1992) Effect of D-amino acids on structure and synthesis of peptidoglycan in *Escherichia coli, J Bacteriol* 174, 5549-5559.
17. Lam, H., Oh, D. C., Cava, F., Takacs, C. N., Clardy, J., de Pedro, M. A., and Waldor, M. K. (2009) D-amino acids govern stationary phase cell wall remodeling in bacteria, *Science* 325, 1552-1555.
18. Cava, F., de Pedro, M. A., Lam, H., Davis, B. M., and Waldor, M. K. (2011) Distinct pathways for modification of the bacterial cell wall by non-canonical D-amino acids, *EMBO J.* 30, 3442-3453.
19. Sletten, E. M., and Bertozzi, C. R. (2009) Bioorthogonal chemistry: fishing for selectivity in a sea of functionality, *Angew Chem Int Ed Engl* 48, 6974-6998.
20. Thompson, R. J., Bouwer, H. G., Portnoy, D. A., and Frankel, F. R. (1998) Pathogenicity and immunogenicity of a *Listeria monocytogenes* strain that requires D-alanine for growth, *Infect Immun* 66, 3552-3561.
21. Kiick, K. L., Weberskirch, R., and Tinell, D. A. (2001) Identification of an expanded set of translationally active methionine analogues in *Escherichia coli, FEBS Lett* 502, 25-30.
22. Kiick, K. L., Saxon, E., Tinell, D. A., and Bertozzi, C. R. (2002) Incorporation of azides into recombinant proteins for chemoselective modification by the Staudinger ligation, *Proc Natl Acad Sci USA* 99, 19-24.
23. Neuhaus, F. C., and Baddiley, J. (2003) A continuum of anionic charge: structures and functions of D-alanyl-teichoic acids in gram-positive bacteria, *Microbiol Mol Biol Rev* 67, 686-723.
24. Webb, A. J., Karatsa-Dodgson, M., and Grundling, A. (2009) Two-enzyme systems for glycolipid and polyglycerolphosphate lipoteichoic acid synthesis in *Listeria monocytogenes, Mol Microbiol* 74, 299-314.
25. Kamisango, K., Fujii, H., Okumura, H., Saiki, I., Araki, Y., Yamamura, Y., and Azuma, I. (1983) Structural and immunochemical studies of teichoic acid of *Listeria monocytogenes, J Biochem* 93, 1401-1409.
26. Eugster, M. R., and Loessner, M. J. (2011) Rapid analysis of *Listeria monocytogenes* cell wall teichoic acid carbohydrates by ESI-MS/MS, *PLoS One* 6, e21500.
27. Lupoli, T. J., Tsukamoto, H., Doud, E. H., Wang, T. S., Walker, S., and Kahne, D. (2011) Transpeptidase-mediated incorporation of D-amino acids into bacterial peptidoglycan, *J Am Chem Soc* 133, 10748-10751.
28. Korsak, D., Markiewicz, Z., Gutkind, G. O., and Ayala, J. A. (2010) Identification of the full set of *Listeria monocytogenes* penicillin-binding proteins and characterization of PBPD2 (Lmo2812), *BMC Microbiol* 10, 239.
29. Korsak, D., Popowska, M., and Markiewicz, Z. (2005) Analysis of the murein of a *Listeria monocytogenes* EGD mutant lacking functional penicillin binding protein 5 (PBP5), *Pol J Microbiol* 54, 339-342.
30. Boneca, I. G., Dussurget, O., Cabanes, D., Nahori, M. A., Sousa, S., Lecuit, M., Psylinakis, E., Bouriotis, V., Hugot, J. P., Giovannini, M., Coyle, A., Bertin, J., Namane, A., Rousselle, J. C., Cayet, N., Prevost, M. C., Balloy, V., Chignard, M., Philpott, D. J., Cossart, P., and Girardin, S. E. (2007) A critical role for peptidoglycan N-deacetylation in *Listeria* evasion from the host innate immune system, *Proc Natl Acad Sci USA* 104, 997-1002.
31. Yao, J. Z., Uttamapinant, C., Poloukhtine, A., Baskin, J. M., Codelli, J. A., Sletten, E. M., Bertozzi, C. R., Popik, V. V., and Ting, A. Y. (2012) Fluorophore targeting to cellular proteins via enzyme-mediated azide ligation and strain-promoted cycloaddition, *J Am Chem Soc* 134, 3720-3728.
32. Beatty, K. E., Liu, J. C., Xie, F., Dieterich, D. C., Schuman, E. M., Wang, Q., and Tirrell, D. A. (2006) Fluorescence visualization of newly synthesized proteins in mammalian cells, *Angew Chem Int Ed Engl* 45, 7364-7367.
33. Miner, M. D., Port, G. C., and Freitag, N. E. (2008) Functional impact of mutational activation on the *Listeria monocytogenes* central virulence regulator PrfA, *Microbiology* 154, 3579-3589.
34. Zeldovich, V. B., Robbins, J. R., Kapidzic, M., Lauer, P., and Bakardjiev, A. I. (2011) Invasive extravillous trophoblasts restrict intracellular growth and spread of *Listeria monocytogenes, PLoS Pathog* 7, e1002005.
35. Rafelski, S. M., and Theriot, J. A. (2006) Mechanism of polarization of *Listeria monocytogenes* surface protein ActA, *Mol Microbiol* 59, 1262-1279.
36. Jewett, J. C., Sletten, E. M., and Bertozzi, C. R. (2010) Rapid Cu-free click chemistry with readily synthesized biarylazacyclooctynones, *J Am Chem Soc* 132, 3688-3690.
37. Baskin, J. M., Prescher, J. A., Laughlin, S. T., Agard, N. J., Chang, P. V., Miller, I. A., Lo, A., Codelli, J. A., and Bertozzi, C. R. (2007) Copper-free click chemistry for dynamic in vivo imaging, *Proc Natl Acad Sci USA* 104, 16793-16797.
38. Breidenbach, M. A., Gallagher, J. E., King, D. S., Smart, B. P., Wu, P., and Bertozzi, C. R. (2010) Targeted metabolic labeling of yeast N-glycans with unnatural sugars, *Proc Natl Acad Sci USA* 107, 3988-3993.
39. Saxon, E., and Bertozzi, C. R. (2000) Cell surface engineering by a modified Staudinger reaction, *Science* 287, 2007-2010.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present inven-

What is claimed is:

1. An isolated, modified peptidoglycan (PG) comprising at least one modified D-amino acid chemically conjugated to a reagent via a heterocycle, wherein the modified D-amino acid is an azide-modified, an alkyne-modified, or a norbornene-modifed D-amino acid, and the reagent is an azide-containing reagent, an alkynyl reagent or a norbornene-reactive reagent.

2. The isolated, modified PG of claim 1, wherein the reagent comprises a detectable label.

3. The isolated, modified PG of claim 1, wherein the reagent comprises a therapeutic agent.

4. The isolated, modified PG of claim 1, wherein the reagent comprises an immunomodulatory molecule.

5. A composition comprising:
a) an isolated, modified peptidoglycan comprising at least one modified D-amino acid, wherein the modified D-amino acid is chemically conjugated to a reagent selected from an azide-containing reagent, an alkynyl reagent and a norbornene-reactive reagent, and the isolated, modified peptidoglycan is described by the formula:

$PG-L^1-Z-L^2-Y$ wherein:
PG is the modified peptidoglycan, $L^1$ and $L^2$ are independently optional linkers, Z is a heterocycle, and Y is a therapeutic agent or an immunomodulatory molecule; and
b) a pharmaceutically acceptable excipient.

6. The composition of claim 5, wherein Y is a therapeutic agent.

7. The composition of claim 5, wherein Y is an immunomodulatory molecule.

8. The composition of claim 7, wherein Y is an antigen.

9. The isolated, modified PG of claim 1, wherein the modified D-amino acid is an azide-modified D-amino acid, and the reagent is an alkynyl or phosphine reagent.

10. The isolated, modified PG of claim 1, wherein the modified D-amino acid is an alkyne-modified D-amino acid, and the reagent is an azide or alkynyl reagent.

11. The isolated, modified PG of claim 1, wherein the modified D-amino acid is a norbornene-modified D-amino acid, and the reagent is a norbornene-reactive agent.

12. The composition of claim 2, wherein the detectable label is a fluorophore.

13. The isolated, modified PG of claim 2, wherein the detectable label is a radioactive isotope.

14. The isolated, modified PG of claim 2, wherein the detectable label is biotin.

15. The isolated, modified PG of claim 2, wherein the detectable label is a peptide that can be detected by antibody binding.

* * * * *